(12) United States Patent
Schaefer et al.

(10) Patent No.: US 9,849,453 B2
(45) Date of Patent: Dec. 26, 2017

(54) METHOD FOR PROCESSING A FLUID AND FLUID PROCESSING DEVICE

(71) Applicant: QIAGEN GmbH, Hilden (DE)

(72) Inventors: Andreas Schaefer, Leverkusen-Schlebusch (DE); Thomas Voit, Hilden (DE); Markus Zbinden, Engelburg (CH); Andreas Schmiede, Neuchâtel (CH)

(73) Assignee: QIAGEN GMBH, Hilden (DE)

( * ) Notice: Subject to any disclaimer, the term of this patent is extended or adjusted under 35 U.S.C. 154(b) by 535 days.

(21) Appl. No.: 14/295,689

(22) Filed: Jun. 4, 2014

(65) Prior Publication Data

US 2014/0349410 A1 Nov. 27, 2014

Related U.S. Application Data

(62) Division of application No. 11/992,616, filed as application No. PCT/EP2006/066759 on Sep. 26, 2006, now Pat. No. 8,771,614.

(30) Foreign Application Priority Data

Sep. 26, 2005 (EP) ..................................... 05020848

(51) Int. Cl.
*B01L 3/00* (2006.01)
*B01L 9/06* (2006.01)
(Continued)

(52) U.S. Cl.
CPC ......... *B01L 3/5021* (2013.01); *B01L 3/50255* (2013.01); *B01L 3/56* (2013.01);
(Continued)

(58) Field of Classification Search
CPC .. B01L 3/5021; B01L 3/5025; B01L 3/50255; B01L 2200/023; B01L 2300/041;
(Continued)

(56) References Cited

U.S. PATENT DOCUMENTS 3,679,129 A 7/1972 Livshitz et al.
3,905,772 A 9/1975 Hartnett et al.
(Continued)

FOREIGN PATENT DOCUMENTS

DE 3101231 A1 11/1981
DE 3425922 A1 1/1986
(Continued)

OTHER PUBLICATIONS

International Preliminary Report on Patentability for PCT/EP2006/066759 dated Mar. 26, 2008 (8 Pages).
(Continued)

*Primary Examiner* — Timothy Cleveland
(74) *Attorney, Agent, or Firm* — McBee Moore Woodward & Vanik IP, LLC; Susan McBee

(57) ABSTRACT

The present invention relates to improved methods for processing fluids and to a fluid processing device (1) for use in a centrifuge comprising: (a) a first holder (14) form-fit to the shape of a first tube (18) for holding said first tube (18) whereby said first tube (18) has a first cross section (A1); and (b) a second holder (22) form-fit to the shape of a second tube (26) for holding said second tube (26) whereby said second tube (26) has a second cross section (A2) that is different from said first cross section (A1). With the fluid processing devices and the methods according to the invention, it is possible to simplify the centrifugal processing steps for a given fluid processing sequence and to automate them.

12 Claims, 25 Drawing Sheets

(51) Int. Cl.
  *B04B 5/04* (2006.01)
  *G01N 1/40* (2006.01)
  *B04B 5/02* (2006.01)
  *G01N 35/00* (2006.01)
(52) U.S. Cl.
  CPC *B01L 9/06* (2013.01); *B04B 5/02* (2013.01); *B04B 5/0421* (2013.01); *G01N 1/405* (2013.01); *G01N 1/4077* (2013.01); *B01L 2200/023* (2013.01); *B01L 2400/0409* (2013.01); *B04B 2005/0435* (2013.01); *G01N 2035/00485* (2013.01); *G01N 2035/00504* (2013.01); *Y10T 436/25375* (2015.01)
(58) Field of Classification Search
  CPC ......... B01L 2300/042; B01L 2300/043; G01N 1/4077; B04B 5/02; B04B 5/0421; B04B 2005/0435
  See application file for complete search history.

(56) References Cited

U.S. PATENT DOCUMENTS

| | | | |
|---|---|---|---|
| 4,482,522 A | 11/1984 | Baudisch et al. | |
| 4,683,058 A | 7/1987 | Lyman et al. | |
| 4,956,148 A * | 9/1990 | Grandone | B01L 3/5025 206/561 |
| 5,166,889 A | 11/1992 | Cloyd | |
| 5,178,602 A | 1/1993 | Wells | |
| 5,665,047 A | 9/1997 | Brimhall | |
| 6,060,022 A | 5/2000 | Pang et al. | |
| 2005/0208548 A1 | 9/2005 | Block et al. | |
| 2007/0161491 A1 | 7/2007 | Jinno et al. | |

FOREIGN PATENT DOCUMENTS

| | | |
|---|---|---|
| DE | 2002004005821 U1 | 9/2004 |
| EP | 0142704 A1 | 5/1985 |
| EP | 0884104 A1 | 12/1998 |
| WO | 2005030399 A1 | 4/2005 |

OTHER PUBLICATIONS

EPO Office Action in EP 06 806 837.8 dated Jul. 13, 2012 (5 pages).
International Search Report of PCT/EP2006/066759 dated Nov. 16, 2006 (4 pages).
Chinese Office Action dated Dec. 21, 2011 on related Chinese Application No. 200680043902.7 and English Translation thereof (12 pages).

* cited by examiner

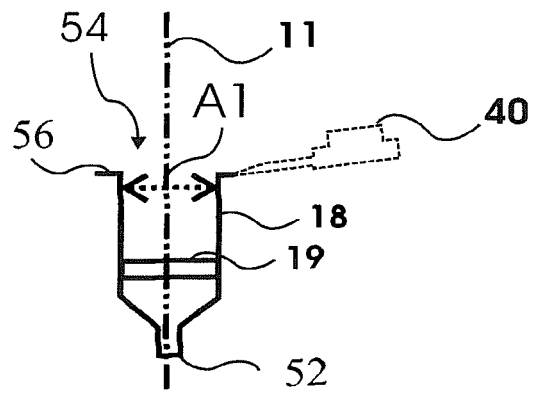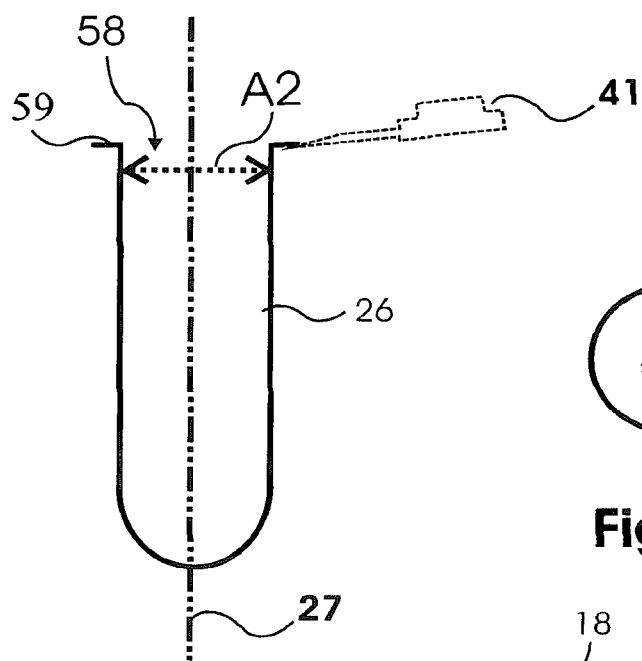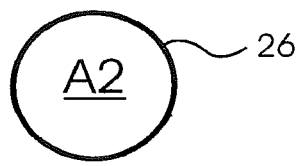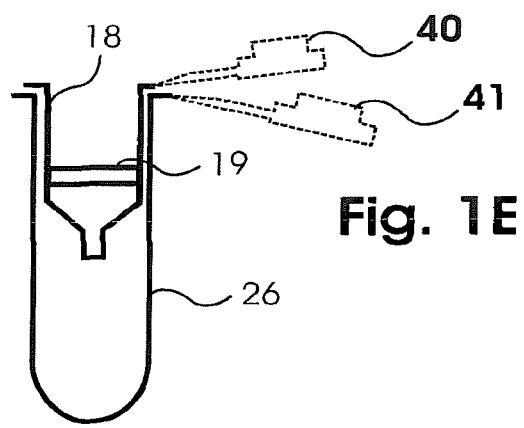

Fig. 2A
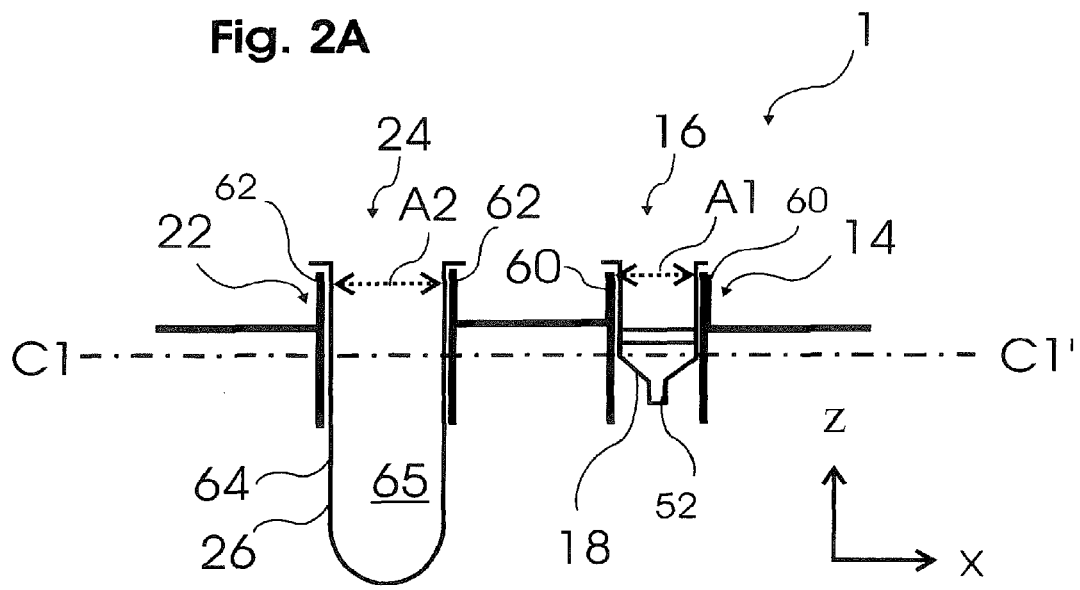
Fig. 2B
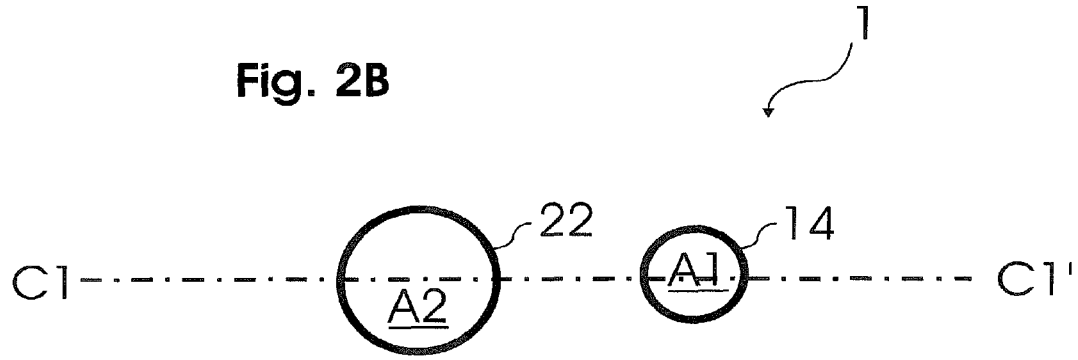
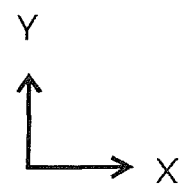

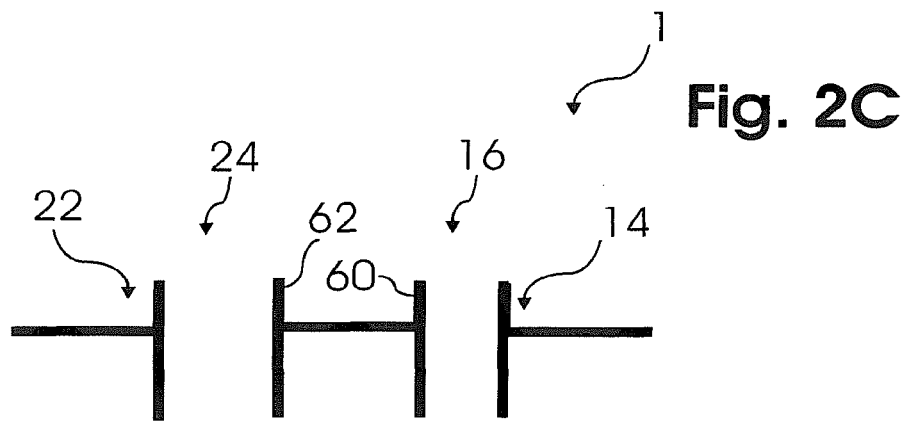
Fig. 2C
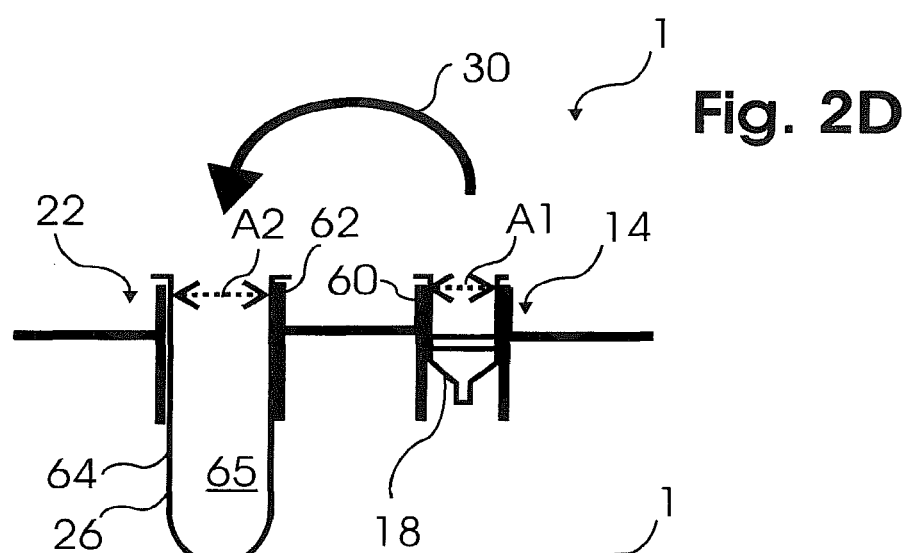
Fig. 2D
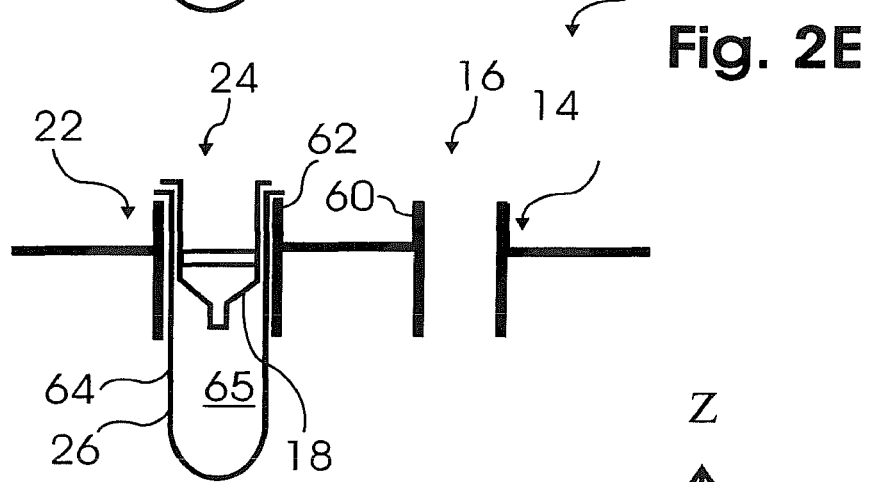
Fig. 2E
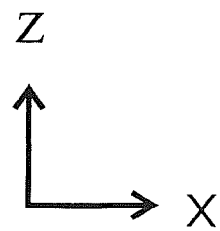

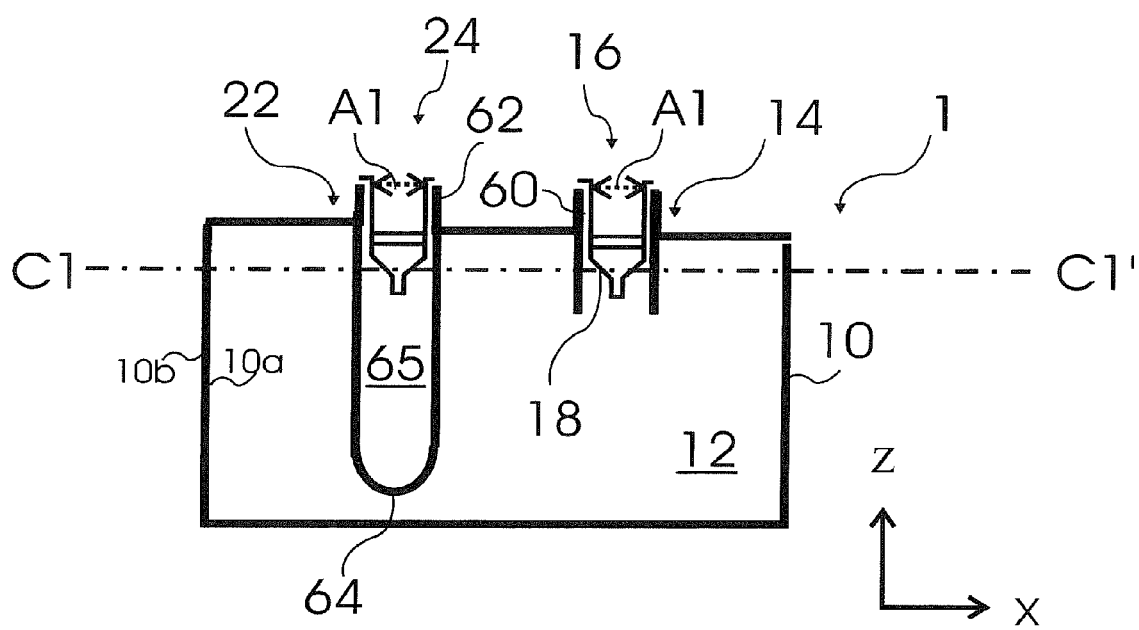
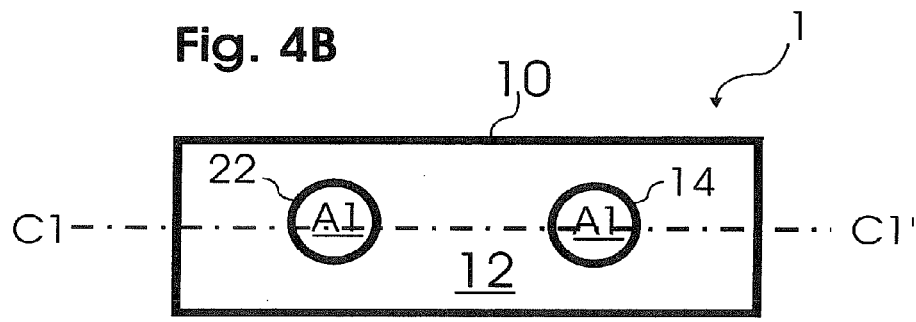
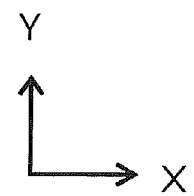

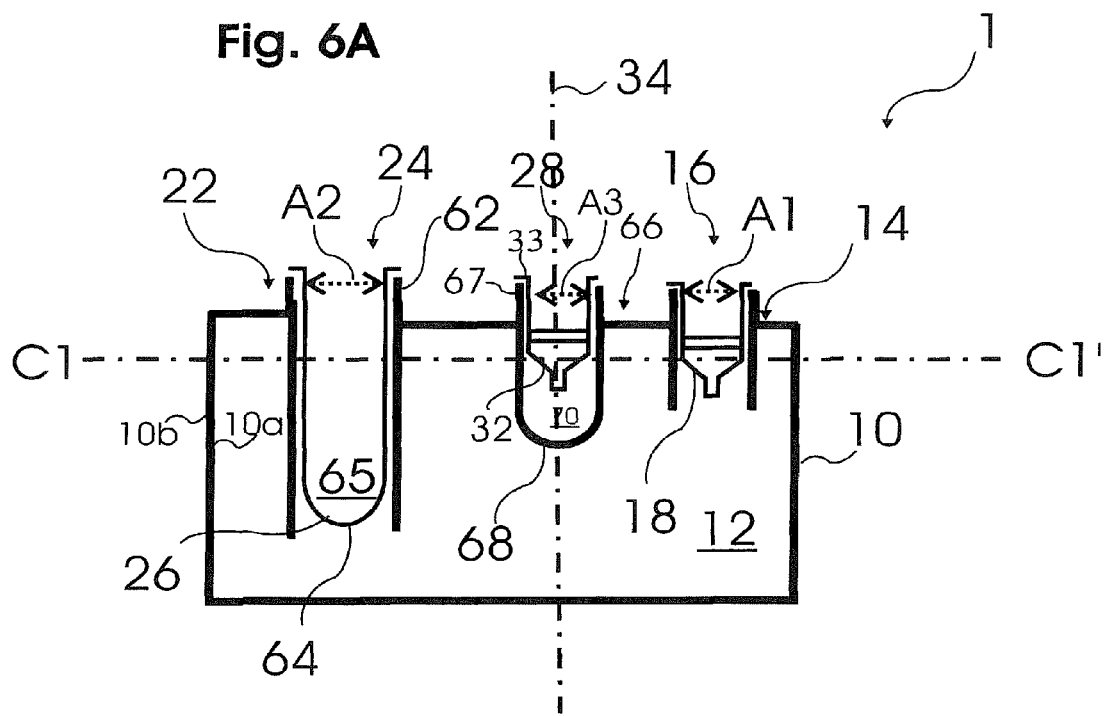
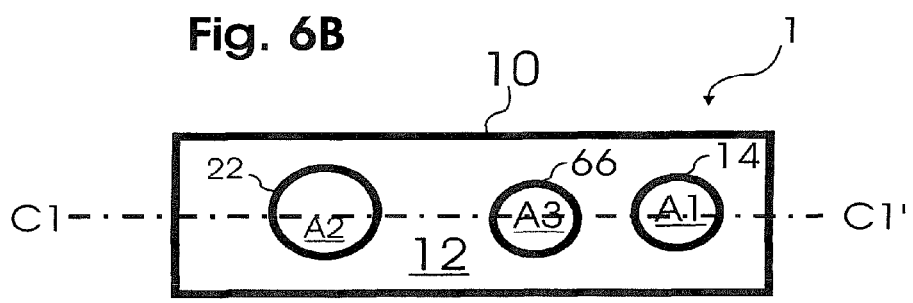

METHOD FOR PROCESSING A FLUID AND FLUID PROCESSING DEVICE

CROSS REFERENCE TO RELATED APPLICATIONS

This application is a divisional of U.S. Ser. No. 11/992,616, filed Sep. 15, 2009, which is a National Stage filing under 35 U.S.C. §371 of International Application No. PCT/EP2006/066759, filed Sep. 26, 2006, which claims priority to European Application No. 05020948.5, filed Sep. 26, 2005, the contents of which are incorporated herein by reference in their entireties.

BACKGROUND OF THE INVENTION

Field of the Invention

The present invention relates to a fluid processing device and a method for processing a fluid. In particular, the present invention relates to a device and a method for preparing biomolecules including but not limited to nucleic acids, proteins, peptides, polypeptides, nucleotides, and lipids.

In many technical fields, like chemistry, biology, medicine or environmental protection, fluids have to be analyzed, processed, or brought into reaction with each other. For this purpose, fluids are filtered, cooled, heated, decomposed, washed, pipetted, or treated by other procedures. Often, in order to prepare a fluid, it is necessary to go through a long sequence of fluid processing steps. Further, in many cases, large sets of different fluids need to be processed according to the same sequence or batches of the same fluid need to be processed in parallel. This may be time consuming, limit the throughput and be prone to errors occurring during the procedure.

Fluid processing is used, for example, in the field of extracting and/or purifying biomolecules like nucleic acids or proteins. For example, a widely known method of purifying biomolecules is based on the steps of generating access to the content of a biological sample ("lysis"), selective binding of components of the content of the biological sample to a solid support or carrier material ("binding"), removing unwanted components from the solid support or carrier material ("washing"), and eluting the component of interest ("elution").

In order to allow for a selective adsorbing and desorbing in the process of biomolecules purification, filter elements made of, e.g., silica-gel have been developed that on the one hand are porous or matrix-like in order to allow a fluid to pass through the filter element, and that on the other hand have a surface to which the biomolecules bind in a specific or nonspecific process. In other purification procedures biomolecules are detained on filter elements simply by the principle of size exclusion. In either way, if a biomolecule, e.g. a nucleic acid containing fluid passes through the filter element, some or all of the content remains with the filter element while the rest passes through the filter element.

Further, in order to recover the biomolecule from the filter element, an elution fluid, e.g. nuclease-free water, is dispensed onto the filter element for desorbing the biomolecule. This way, the biomolecule of interest is eluted from the filter element to be collected in a collection tube. Such filter elements are often applied as membranes either implemented in single tubes having an inlet opening and an outlet opening, or in multiwell plates, and processed using centrifuges ("spin format") or vacuum based apparatuses. Single tubes with an inlet opening and an outlet opening that have a membrane and that can be spun in a centrifuge are also known as columns, spin columns, or single spin columns.

In general, the advantages of centrifuge based procedures over vacuum based methods are higher purity, higher concentration and a lower potential of cross contamination. In general, the best results for the purification of biomolecules, with regard to quality and concentration can be achieved using single spin columns combined with high g forces (>10.000×g) as there is a minimum of cross contamination and a maximum recovery from the membrane. A drawback is the labor intensive manual handling of spin columns increasing the error proneness and the process time if different samples are to be treated or processed simultaneously. A higher degree of standardization and automation as well as a higher throughput can be achieved by using multiwell plate formats mostly at the cost of quality and/or quantity.

QIAGEN offers a wide range of purification protocols for different biomolecules from a variety of biological samples all based on the overall Bind-Wash-Elute principle by using different filter materials and devices as, for example, described in WO 03/040364 or U.S. Pat. No. 6,277,648. The commercially available product "QIAGEN QIAprep Spin Miniprep Kit" for example discloses a typical purification sequence and offers standardized QIAprep Spin columns and 2 ml collection tubes for use in a centrifuge, and several reagents and buffers.

There are several publications relating to the automated processing of fluids involving centrifugal steps. U.S. Pat. No. 4,344,768 describes a pipettor apparatus for automatically transferring accurate and precise multiple quantities of samples (e.g., blood serum) and reagent to the rotatable transfer disc of a centrifugal analyzer. EP 0 122 772 describes a chemical manipulator adapted to automate the analysis of liquids of a μl unit, such as a DNA sample. U.S. Pat. No. 6,060,022 describes an automated sample processing system including an automatic centrifuge device. GB 535,188 describes an apparatus for obtaining a plurality of working bucket angles at a given speed of rotation of a centrifuge.

U.S. Pat. No. 5,166,889 describes a sampling system adapted for blood, wherein a plurality of sample tubes are positioned for ready access on a support wheel, EP 569 115 A3 describes a centrifuge-based device for preparing DNA, and U.S. Pat. No. 539,339 describes an integral biomolecule preparation device using a centrifuge.

Several apparatuses for the preparation of samples using centrifugation are commercially available. "GENTRA Autopure LS" (GENTRA) and "AutoGenflex 3000" (AutoGen) are automated systems with an integrated centrifuge for the isolation of e.g. DNA after precipitation without using filtration elements. "DNA-Spinner" (PerkinElmer), "Genesis FE 500" (Tecan) and Microlab STARplus (Hamilton) are examples for more open systems where a liquid handling instrument is combined with an automated centrifuge for the use of multiwell plates.

On the other hand, for example, the "BioRobot 3000/8000" (QIAGEN) can be used for the preparation of samples, e.g. nucleic acids, in a 96-well format using vacuum filtration whereas the "Fuji QuickGene 800" applies a low pressure filtration principle on single columns.

However, most existing integrated systems for an automated preparation of biomolecules from fluids applying centrifugation are designed for a preparation of only specific procedures. Other instrument setups comprising an automated centrifuge are optimized for high throughput preparations using multiwell filtration plates. A drawback of existing automation systems is their inability to process high quality preparation procedures based on spin-columns without manual interventions.

SUMMARY OF THE INVENTION

In order to overcome one or several of the above mentioned problems, and in order to improve known methods of processing fluids, fluid processing devices according to the independent claims 1, 8, 14, 21, 27, and 35, a rotor according to independent claim 74, and methods for processing a fluid according to the independent claims 77 and 79 are provided.

Further aspects, improvements and variations of the invention are disclosed in the dependent claims, the figures and the description.

With the fluid processing devices according to the claims 1, 8, 14, 21, 27 and 35, and with the methods according to the claims 77 and 79, it is possible to cany out a wide range of different preparation procedures involving one or more tubes (e.g. spin columns, collection tubes etc.) within one and the same fluid processing device. In particular, it is possible to provide for a fully automated and standardized preparation of a variety of biomolecules from fluids using well established procedures and proven spin column based chemistry for low to medium throughput needs, preferably without any manual intervention. For example, the fluid processing device can be used for an automated preparation of biomolecules using filtration elements. It can further be used for an automated processing of the bind-wash-elute steps, or lysing-bind-wash-elute steps, for biomolecule extraction and purification procedures in a single fluid processing device. This enables a one-to-one correspondence between a processed sample and a fluid processing device. Thus, the risk of cross-contamination and misallocation of samples can be minimized.

Further, the automated processes can be carried out with the fluid processing device used as a disposable device. Further, with the fluid processing device having a first holder and a second holder, the tubes (e.g. spin columns and collection tubes) can be uniquely assigned to respective positions on the fluid processing device so that cross-contamination and likelihood of confusing the tubes can be minimized. At the same time, the fluid processing device according to the invention provides a platform for a large variety of preparations procedures. It can further be used for automatically handle multiple individual tubes or spin columns in parallel in order to reach high standardization analogues to multiwell formats. Further, it is possible to provide a device and a method for automated and standardized preparation of a variety of biomolecules from fluids using well established procedures and proven spin column based chemistry for low to medium throughput needs.

According to a first aspect of the invention, a fluid processing device is provided having a first holder for holding a first tube having a first cross section, and a second holder for holding a second tube having a different second cross section. This may help to increase throughput by centrifuging different types of tubes at a time in order to carry out different fluid processing steps at a time. For example, if the first tube is a filter tube for filtering a fluid during centrifugation and the second tube is a collection tube for holding a fluid during centrifugation, filtering and pelleting of different fluids may be carried out in only one centrifuging step.

Further, if the first tube and the second tube are geometrically adapted to each other so that the first tube can be inserted into the second tube, the fluid processing device can be prepared such that two different processing steps within a centrifuge can be carried out in a row by transferring the first tube directly from the first holder to the second holder. This saves time, reduces error proneness and eliminates the risk of cross contamination compared to the case where before each processing step in a centrifuge, the tubes need to be prepared outside the centrifuge and returned into the centrifuge. For example, by providing the first holder with a first tube used for fluid filtering and the second holder with a second tube used for fluid collection, the change from fluid filtering to fluid collection may be carried out by simply transferring the first tube from the first holder to the second tube held by the second holder.

In particular, with the first tube having a filter element for binding biomolecules, the first holder can be used for holding the first tube to perform a binding and one or several washing steps while, by transferring the first tube from the first holder to the second holder holding a second tube, the second holder can be used for holding the second tube for collecting the purified biomolecules eluted from the first tube. This way, with the fluid processing device according to the invention, binding, multiple washing and elution steps can be carried out in a row within the centrifuge without having to move the first tube out and back into the centrifuge for inserting the first tube into a collection tube. Thus, the risk of cross contamination due to splashes from droplets at the outlet of filter tubes during tube transfer steps from and to the centrifuge can be eliminated.

Preferably, the fluid processing device comprises a first container having a first container volume for holding a fluid whereby, preferably, the first holder is arranged with respect to the first container such that a fluid flowing through the first tube flows into the first container. With the first container, it is possible to collect the fluids that may have passed through the first tube to reduce cross contamination with, e.g., samples of adjacent tubes within the centrifuge. In particular, with a sufficiently large first container volume, larger amounts of waste fluids originating from the binding step and the washing step can be discarded iri the first containers. This saves additional time consuming waste disposal steps and reduces the number of unloading and reloading steps for unloading and reloading the centrifuge. Further, while a large first container volume is generally desired, it is generally preferred that the first container is arranged with respect to the first holder so that the dimension of the fluid processing device as a whole is sufficiently small to be also usable in small centrifuges. It is further preferred that the first holder is arranged with respect to the first container in a way that a first tube held by the first holder does not come in contact with the fluid in the first container at any step of the process.

Further, according to one aspect of the present invention, the first holder is form-fit to the shape of the first tube and the second holder is form-fit to the shape of the second tube to provide for a secure holding of the first tube with respect to the second tube during centrifugation of the fluid processing device.

According to a further aspect of the invention, the first container has a first container volume that is different from a second container volume into which a fluid flows that flows through the first tube held by the second holder at a second position. This way, it is possible to provide for a large first container volume for collecting large volumes of fluids that flow through the first tube during the binding and washing steps while using only a small second container volume for collecting the purified biomolecule during elution. By having the container volumes adjusted to the actual needs of a given processing sequence, over-sizing of the equipment that needs to be centrifuged can be avoided which in turn facilitates the use of smaller, less expensive centrifuges.

According to a further aspect of the invention, a first container is provided that has a container volume with a container cross section that is at least ten percent larger than the first cross section of the first tube. Preferably, the container cross section is taken in a plane parallel to the first cross section of the first tube when held by the first holder. By providing a larger container cross section compared to the first cross section, the container volume for collecting the fluids originating from the binding and washing steps may be enlarged According to a further aspect of the invention, a first container having an inner surface for defining a first container volume is provided whereby the inner surface adjoins to the second holder. Having the inner surface of the first container extended up to the second holder helps to maximize the first container volume for collecting the fluids originating from the binding and washing steps. By adjoining the inner surface of the first container to the second holder, additional stability of the fluid processing device, e.g., against a centrifugal force, can be provided.

It is a further aspect of the present invention to provide for a holder having a first stopper for holding a first tube and thereby defining a first stopper plane, and to provide for a second holder having a second stopper for holding a second tube and thereby defining a second stopper plane whereby the second stopper plane is different from the first stopper plane. This way, it is possible to hold the first tube at a height different from the height of the second tube as measured along the projections onto the respective tube axes. Holding the first and the second tubes at different heights facilitates easier access to the tubes if the holders are positioned closely with respect to each other. It further provides the opportunity to discriminate between the two holding positions.

It is a further aspect of the present invention to provide for at least one first cap fixture means for holding a first cap of a first tube in a defined position with respect to the first holder during centrifugation. Preferably, the first cap fixture means are arranged such that the first cap is held at a position that leaves the first tube's inlet opening open during centrifugation and makes it accessible to pipetting means. This way, the first tube can be centrifuged with an open inlet opening without having to worry about damage caused by the first tube's first cap hanging loose during centrifugation. An advantage of an open inlet opening of the first tube during centrifugation is that after centrifugation, fluids like, e.g., a wash fluid can be dispensed into the tube without having to remove a cap from the inlet opening.

A further aspect of the present invention is a method including the step of automatically transferring a first tube directly from a first holding position within a centrifuge to a second holding position within the centrifuge. The direct transfer can be used to reduce the steps necessary for purifying biomolecules. It further eliminates errors caused by mix up or misallocation of sample tubes during manual tube transfer steps outside the centrifuge.

A further aspect of the present invention is a method including the step of transferring a first tube from said holder of one of at least one fluid processing device to a second holder of one of said at least one fluid processing device. This way, binding, washing and elution of the biomolecules can be carried out without having to load and unload the centrifuge.

BRIEF DESCRIPTION OF THE DRAWINGS

The following figures below disclose several embodiments according to the invention for illustrational purposes only. In particular, the disclosure within the figures is not meant to limit the range of protection of the invention:

FIGS. 1A-1B: a first tube having an inlet opening and an outlet opening

FIGS. 1C-1E a second tube having an inlet opening that is sized to receive the first tube;

FIGS. 2A-2E: A first fluid processing device according to the invention for holding a first tube and a second tube having different cross sections;

FIGS. 4A-4E: A third fluid processing device according to the invention for holding a first tube whereby the fluid processing device has a first container and a second container of different size;

FIGS. 6A-6E: A fifth fluid processing device according to the invention for holding a first tube, a second tube and a third tube having at least two different cross sections whereby the fluid processing device has a first container;

DETAILED DESCRIPTION OF THE INVENTION

Figure 3A:
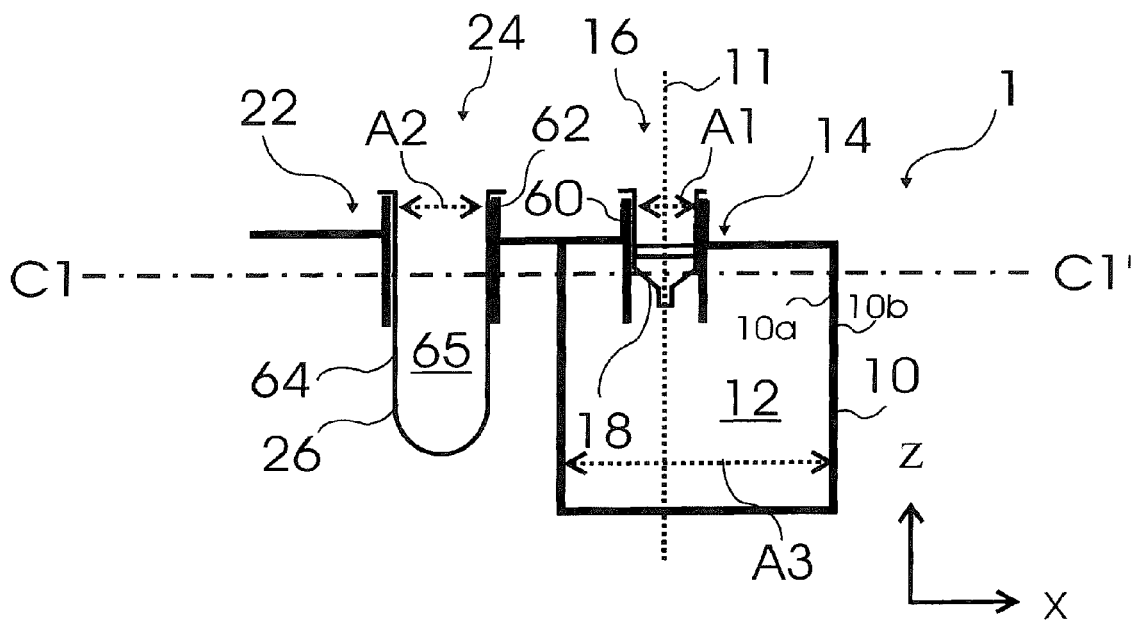
FIGS. 3A-3E: A second fluid processing device according to the invention for holding a first tube and a second tube having different cross sections whereby the fluid processing device has a first container.

It is one aspect of the present invention to improve methods of processing fluids that use centrifuges. For that purpose, the present invention provides fluid processing devices for use in a centrifuge. A fluid may be anything that is liquid independent of whether that liquid has a high or low viscosity, or contains particles or solid elements moving within the liquid. The fluid processing devices according to the invention may be used to manipulate or treat fluids by processes such as filtering fluids, adsorbing specific elements of fluids to specific materials, desorbing specific elements from specific materials, separating components from fluids, collecting manipulated fluids, or dumping waste fluids. Preferably, the fluid processing devices according to the invention are used to purify biomolecules such as nucleic acids, proteins, peptides, polypeptides, nucleotides, and lipids.

In order to be usable in a centrifuge, it is further preferred that the fluid processing device is connectable to the rotor of the centrifuge. By having the centrifuge rotate the rotor, a centrifugal force can be applied to the fluid processing device. Preferably, the connection to the rotor is realized by connection means that may be part of the fluid processing device or not. If the connection means are not part of the fluid processing device, it is preferred that the connection means have a holding structure for removably holding the fluid processing device. In this case, and if the fluid processing device includes a first container, the elements that are integrally connected with the first container form a unit that is below referred to as first container comprising structure.

A holding structure for removable holding the fluid processing device may be realized in different ways that are known in the art. For example, the holding structure may be form-fit to the outer shape of the fluid processing device so that it can receive and carry the fluid processing device securely even during centrifugation. Other methods for the holding structure to hold the fluid processing device may be clamping, locking and so on.

Independent of whether the connection means are part of the fluid processing device or not, it is preferred that the connection means facilitate a removable connection of the fluid processing device with the rotor. This way, it is possible to connect a fluid processing device to the rotor for carrying out a centrifugal step and, thereafter, to remove the fluid processing device from the centrifuge to perform further steps with the fluids outside of the centrifuge. In particular, by having the fluid processing device being removably connectable to the rotor, the fluid processing devices may be used as disposables. Having disposable fluid processing devices helps reducing sample contamination caused by reuse and increasing process safety and safety for the operating personnel. Further it may save time as loading of the fluid processing devices needed for the next processing sequence can be performed outside the centrifuge during an ongoing processing sequence.

It is further preferred that the fluid processing device is small compared to the rotor so that multiple fluid processing devices can be connected to the rotor at a time. This way, multiple fluid samples can be centrifuged at a time within a centrifugal step to increase through-put. Also, if the fluid processing devices are used as disposables, i.e. as a one-time-use article, it may save costs to keep the fluid processing devices small.

According to one aspect of the invention, the fluid processing device includes a first holder for holding a first tube and a second holder for holding a second tube. Preferably, the first holder is capable of holding the first tube at a first holding position with respect to the second holder, preferably at rest and during centrifugation. Analogously, it is preferred that the second holder is capable of holding the second tube at a second holding position with respect to the first holder, at rest and during centrifugation. Therefore, it is preferred that the first holder and the second holder are rigidly connected with each other. Further, it is preferred that at least one of the first holder and the second holder is made of one piece in order to better withstand deformation during centrifugation. It is further preferred that the first and second holders are arranged with respect to each other such that, if they hold a respective first and second tube, the two tubes are aligned in parallel. This way, it is easier to dispense fluids into the respective tubes, or to place first and second tubes into respective first and second holders.

It is generally preferred that at least one of the first holder and the second holder hold a respective first or second tube by mechanical means. Preferably, at least one of the first holder and the second holder is form-fit to the shape of the respective first tube or second tube for holding respective first or second tube. For example, if the first tube has a cylindrical shape and a coaxial collar-like shaped rim (first collar), it is preferred that the first holder has a first cylindrically-shaped inner face form-fit to the outer face of the first tube. This way, the first tube can be slid into the first holder in which case the first tube's holding position is defined within a plane orthogonal to the sliding direction. Further, preferably, the first and the second holder are rigid enough that they can hold a tube during centrifugation in a defined position at all swinging angles αs at which the fluid processing device may be operated.

Further, it is preferred that the first holder provides for a first stopper that stops the sliding of the first tube into the first holder, e.g., by an engagement of the stopper with the first collar of the first tube. This way, the first holding position of the first tube is defined in sliding direction. Further, with the first stopper stopping the sliding in one direction only, the first tube is removably connected with the first holder, i.e. the first tube can easily be slid out of the first holder again any time if needed. With the stopper and the cylindrically-shaped inner face of the first holder, the first holding position of the first tube can be maintained also during centrifugation provided that the centrifugal force has a component pointing into the sliding direction.

Similarly, if the second tube has a cylindrical shape and a coaxial collar-like shaped rim, it is preferred that the second holder has a cylindrically-shaped inner face form-fit to the outer face of the second tube. This way, the second tube can be slid into the second holder in which case the second tube's holding position is defined within a plane orthogonal to the sliding direction.

Further, it is preferred that the second holder provides for a second stopper that stops the sliding of the second tube by an engagement of the stopper with the coaxial collar-like shaped rim (second collar) of the second tube. This way, the second holding position of the second tube is defined within the sliding direction. Further, with the second stopper stopping the sliding in one direction only, the second tube is removably connected with the second holder, i.e. the second tube can easily be slid out of the second holder again any time if needed. With the stopper and the cylindrically-shaped inner face of the second holder, the second holding position of the second tube can be maintained as long as centrifugal and/or gravitational force has a component pointing into the sliding direction.

The use of the words "first tubes" and "second tubes" is to be understood in a broad sense. A tube can be any container in which a fluid can be dispensed through an inlet opening. Preferably, the first tube and the second tube are rotationally symmetrical with respect to respective first or second axes. For example, a tube may have a cylindrical shape having an inlet opening at one end, a conical shape having an inlet opening at one end, or a combination thereof. Further, the cylindrical or conical shapes may have cross sections orthogonal to respective first or second axis that are circular, elliptical, squared, rectangular or combinations thereof. Preferably, the first cross section of the first tube is defined at the first tube's position where the first tube is held by the first holder. Analogously, it is preferred that the second cross section of the second tube is defined at the second tube's position where the second tube is held by the second holder.

Preferably, the first cross section of the first tube and the second cross section of the second tube are adapted to each other such that the first tube can be slid into the second tube via the inlet opening of the second tube. It is further preferred that the outer face of the first tube is form-fit to the inner face of the second tube. This way, the second tube can be used as a holder for holding the first tube during centrifugation. Even more, with the second holder holding a second tube and the second tube holding a first tube, the second holder of the fluid processing device can be used for holding the first tube during centrifugation. In this case it is preferred that the cross section of the first cylindrically-shaped inner face of the first holder is smaller than the cross section of the second cylindrically-shaped inner face of the second holder by not more than 60%, preferably not more than 50%, and even more preferred not more than 40%. On the other hand, in this case, it is preferred that the cross section of the first cylindrically-shaped inner face of the first holder is smaller than the cross section of the second cylindrically-shaped inner face by more than 10%, preferably more than 20%, and even more preferred more than 30%. Preferably, the cross section of the first tube has an area that is larger than 10 mm$^2$, preferably larger than 40 mm$^2$ and possibly larger than 80 mm$^2$. On the other hand, it is preferred that the cross section of the first tube has an area that is smaller than 1000 mm$^2$, preferably smaller than 100 mm$^2$ and possibly smaller than 60 mm$^2$.

In a preferred embodiment of the invention, the first tube has an inlet opening and an outlet opening. Those tubes are also known as columns or spin columns. Further, preferably, the first tube has a filter element separating the inlet opening from the outlet opening. Preferably, the filter element also acts as a membrane for selectively binding biomolecules like nucleic acid. This way, the first tube can be used for a binding step where, by dispensing a biomolecule containing fluid into the inlet opening of the first tube and letting it pass through, biomolecules are selectively bound to the filter element.

On the other hand, it is preferred that the second tube is used for collecting a fluid (collection tube). In this case, it is preferred that the second tube has an inlet opening but no outlet opening. In this case, the second tube can be used for the elution step by collecting the elution fluid including the purified biomolecules that has been eluted from the filter element of the first tube.

In a preferred embodiment of the invention, the fluid processing device includes a first container having a first container volume for holding a fluid. Preferably, the first container is rigidly connected with the first holder. Preferably, the first container is arranged with respect to the first holder such that a fluid flowing through the first tube held by the first holder flows into the first container. Preferably, the fluid flows through the first tube because it is drained by gravitational or centrifugal force. This way, by collecting the fluids that have passed through the first tube into the first container (e.g. a waste fluid during a washing step), cross contamination with adjacent tubes during centrifugation can be eliminated. Further, with a sufficient large first container volume, binding and washing can be carried out without having to interrupt centrifugation for discarding the collected fluid. This helps reducing time consuming unloading and loading steps of the centrifuge, and makes it possible to increase the number of washing steps or to increase the lysate volume. Preferably, the first container volume is larger than 1 ml, preferably larger than 10 ml and possible larger than 50 ml. On the other hand, it is preferred that the first container volume is smaller than 100 ml, preferably smaller than 50 ml and possibly smaller than 10 ml. Preferably, the container volume is defined by the amount of fluid that the first container can hold during centrifugation. On the other hand, the volume of the first container that is actually used for a process, i.e. the net volume of the first container, is preferably smaller than the first container volume by at least 25%, preferably by at least 50%, and even more preferred by at least 75% of the first container volume. This is to avoid that the outlet openings of the first and/or second tubes get in contact with the fluid held within the first container (e.g. waste fluid) during the process in order to prevent contamination of the tubes with the fluid held within the first container and spillage of the fluid during centrifugation.

Preferably, the first container volume is larger than the volume of the second tube to allow for binding and washing steps without interruptions due to discarding the fluid that has flown into the first container. For that purpose, it is preferred that the first container is designed such that the inner surface of the first container adjoins to the second holder. This way, the first container volume can be maximized at a given size of the fluid processing device. Further, in order to maximize the first container volume, it is preferred that the ratio of the weight of the fluid processing device to the volume of the first container is smaller than 10 g/cm$^3$, preferably smaller than 5 g/cm$^3$ and even more preferred smaller than 1 g/cm$^3$. In a preferred embodiment, the fluid processing device weighs 7.23 g and has a container volume of about 11 cm$^3$ which results in a ratio of 0.66 g/cm$^3$.

The following figures disclose schematically some of the embodiments according to the invention in order to illustrate several aspects of the invention. The details and features of the drawings and description, however, should not be understood as limiting the scope of the invention. For example, while the embodiments are disclosed in connection with a particular set of tubes for clarity sakes, the invention is not limited to the use of this particular set of tubes. Also, while the fluid processing device's elements (e.g. the first holder, the second holder, the first container, the second container and so on) in the figures are connected by bold lines, this is merely to be understood schematically to indicate a rigid connection. However, depending on the application and other circumstances, a skilled person understands from the figures that there are many different geometries and shapes in which the fluid processing device's elements can be connected for use in a centrifuge.

FIGS. 1A-1E disclose a first example of a tube set that can be used for purifying biomolecules according to the present invention. The tube set consists of a first tube 18 as shown in FIGS. 1A-1B and a second tube 26 as shown in FIGS. 1C-1D. First tube 18 is rotational symmetric with respect to first axis 11 and has a circular first cross section A1 (see FIG. 1B) in a direction orthogonal to first axis 11. First tube 18 further has a first inlet opening 54, a first outlet opening 52, a filter element 19 through which a fluid that has been dispensed into inlet opening 54 flows in order to reach first outlet opening 52, a collar-like shaped rim (first collar) 56, and, optionally, a first cap 40 that is flexibly connected to collar 56. First cap 40 can be used to close the inlet opening 54 in order to avoid contamination of the tube content. In the case of the tube set of FIGS. 1A-1E, filter element 19 is a matrix material for binding biomolecules, for example nucleic acids, to the filter when a biomolecule containing fluid is dispensed into inlet opening 54.

Second tube 26 of FIGS. 1C-1D is rotational symmetric with respect to second axis 27. Second tube 26 further has circular second cross section A2 (see FIG. 1D) orthogonal to second axis 27, a second inlet opening 58 but no outlet opening (closed tube). Further, second tube 26 has a collar-like shaped rim (second collar) 59 and, optionally, a second cap 41 that is flexibly connected to second collar 59. Second cap 41 is used to close the inlet opening in order to avoid contamination of the tube content. The second cross section A2 of second tube 26 is sized such that first tube 18 can be slid into second tube 26 until first collar 56 of first tube 18 hits second collar 59 of second tube 26 (see FIG. 1E). This way, second tube 26 can be used as a collection tube or container for receiving a fluid dispensed into inlet opening 54 of first tube 18, as well as a holder for holding first tube 18 during centrifugation.

Tubes as shown in FIGS. 1A-1E are commercially available at different sizes and filter materials depending on the application. For example, applicant's QIAprep Spin Miniprep Kit™ offers spin columns (first tubes) having a cross section A1 of 8.8 mm and a length of 30 mm, and collection tubes (second tubes) having a cross section A2 of 10.5 mm and a collection volume of about 2 ml.

FIGS. 2A-2E disclose schematically a first fluid processing device according to the invention. FIG. 2A shows a cross sectional side-view along axis C1-C1' of fluid processing device 1 holding a first tube 18 and a second tube 26 of the types as shown in FIGS. 1 A and 1C. FIG. 2B shows a corresponding cross section along axis C1-C1' in a direction orthogonal to the side view of FIG. 2A. The fluid processing device 1 is comprised of a first holder 14 at a first holding position 16 and a second holder 22 at a second holding position 24 that are rigidly connected with each other. Further, as mentioned before, fluid processing device 1 can be connected to the rotor of a centrifuge by means of connection means (not shown) in ways that will be described later in more details.

As can be seen from FIGS. 2A and 2B, first holder 14 comprises a cylindrically-shaped ring-element having an inner face form-fit to the shape of a portion of first tube 18 to hold first tube 18 at a defined first holding position 16 with respect to the second holder 22. The ring-element of first holder 14 further provides a first stopper 60 which in FIGS. 2A-2E corresponds to the upper rim of the first holder's ring-element. This way, first tube 18 can be slid into the ring-element until first collar 56 of first tube 18 hits the ring-element. This way, first tube 18 is held by first holder 14 as long as gravitational or centrifugal forces have a component in sliding direction, i.e. downward in FIG. 2A Further, first tube 18 can easily be removed from first holder 14 by sliding first tube 18 out of the ring-element. It is self-understood that the cylindrically-shaped ring-element is shaped and rigid enough that it can hold a tube during centrifugation in a defined position at all swinging angles $\alpha$s at which the fluid processing device may be operated.

Similarly, second holder 22 is a cylindrically-shaped ring-element having an inner face form-fit to the shape of a portion of second tube 26 to hold second tube 26 at a defined second holding position 24 with respect to the first holder 14. The ring-element of second holder 22 further provides a second stopper 62 which in FIGS. 2 A-E corresponds to the upper rim of the second holder's ring-element. This way, second tube 26 can be slid into the ring-element until second collar 59 of second tube 26 hits the ring-element. This way, second tube 26 is held by second holder 22 as long as gravitational or centrifugal forces have a component in sliding direction. Further, second tube 26 can easily be removed from second holder 22 by sliding second tube 26 out of the ring-element.

Further, first holder 14 and second holder 22 are each rigidly connected with each other to provide for a sufficient stiffness when being centrifuged. Further, first holder 14 and second holder 22 are oriented with respect to each other such that they hold the two tubes 18, 26 in parallel. A parallel orientation of the first tube and second tube with respect to each other simplifies dispensing of fluids into respective tubes and automatic transfer of the first tube to the second tube.

FIG. 2C illustrates a side view of fluid processing device 1 of FIG. 2A with the first and second tubes removed. Like for the other fluid processing devices in this application, it is preferred that the fluid processing device 1 of FIG. 2C is compression-molded from polymeric material and, preferably, made of one piece in order to improve rigidity and reduce weight and costs.

FIG. 2D-2E illustrate a direct transfer 30 (first tube transfer) of first tube 18 from first holding position 16 to second holding position 24. With the direct transfer 30 and the second tube 26 in place at the second holding position 24, binding and washing steps performed with first tube 18 at first holding position 16 can be followed by an elution step at second holding position 24 without the steps of (a) taking first tube 18 out of the centrifuge for placing the first tube 18 into a second tube; and (b) placing second tube 26 together with first tube 18 back to the centrifuge. Rather, with the fluid processing device of FIGS. 2A-2E, the elution step can be made to follow the binding and washing steps by applying three first tube movements: (a) sliding first tube 18 out of first holder 14, i.e. a movement in axial direction of first tube 18 (z-direction); (b) moving first tube 18 from first holding position 16 to second holding position 24, i.e. a movement lateral to the axial direction (x-direction); and (c) sliding first tube 18 into second tube 26, i.e. a movement in axial direction of first tube 18 (negative z-direction). Accordingly, the direct transfer of first tube 18 includes only two axial movements, one in z-direction and the other in negative z-direction. The way in which first tube 18 is inserted into second tube 26 and held in position has been described earlier in FIGS. 1A-1E.

Further, with first tube 18 placed into second tube 26, elution can be carried out by dispensing an elution fluid into the inlet opening of first tube 18 and carrying out a further centrifugation step. With the centrifuge exerting a centrifugal force in axial direction towards the first tube's outlet opening 52, the elution fluid is pressed through filter element 19, desorbs the bound biomolecules, e.g. nucleic acid, from filter element 19, leaves first tube 18 and is received by second tube 26 which in this case acts as a second container 64 or collection tube. This way, the purified biomolecules are collected in second tube 26 (i.e. second container 64) for further processing. Note that, since second tube 26 can be removed from fluid processing device 1 and since second tube 26 preferably is a standard tube, further processing of the eluate is simpler because of the second tubes compatibility with other lab equipment that may be used for the further processing of the eluate.

Figure 3B:
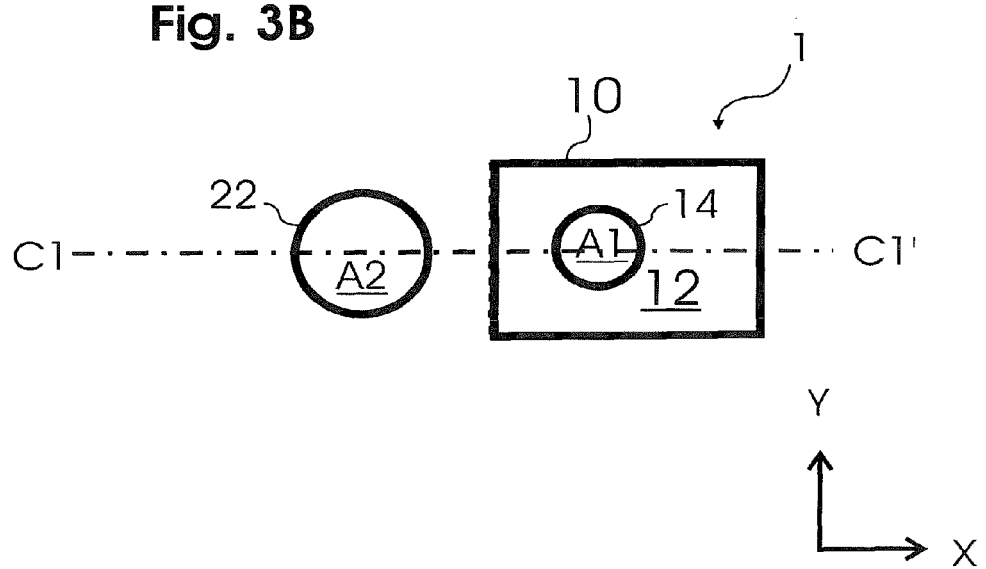
Figure 3C:
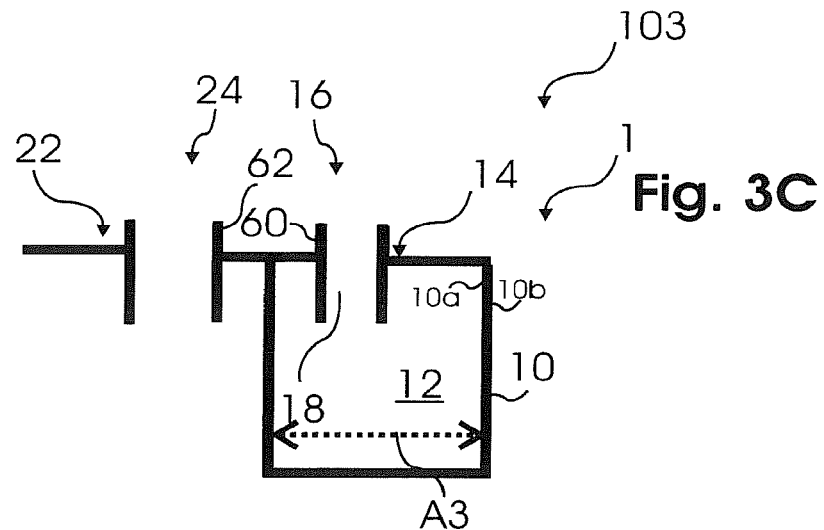

FIGS. 3A-3E disclose schematically a second fluid processing device according to the invention. FIG. 3A shows a cross sectional side-view along axis C1-C1' of the fluid processing device 1 holding a first tube 18 and a second tube 26 of the types as shown in FIGS. 1 A and 1C. FIG. 3B shows a corresponding cross section along axis C1-C1' in a direction orthogonal to the side view of FIG. 3A. The fluid processing device 1 of FIGS. 3A-3E is identical to the one shown in FIGS. 2A-2E except that the fluid processing device 1 of FIGS. 3A-3E has a first container 10 rigidly connected with first holder 14 and second holder 22. First container 10 is positioned with respect to first holder 14 such that a fluid flowing through first tube 18 held by first holder 14 flows into first container 10. This way, fluids (e.g. lysate or wash buffers) that has been dispensed into first tube 18 at first holding position 16 for the binding and washing steps, and that has passed through filter element 19, can be collected within first container volume 12 of first container 10 as waste. First container 10 therefore may also be considered as waste container. By designing first container 10 large enough, binding and washing can be carried out without having to interrupt those processes for discarding the waste. Discarding waste would imply time consuming unloading and reloading of the centrifuge. Further, a sufficiently large waste container 10 allows for additional washing steps etc. without having to go through time consuming waste discarding steps.

First container 10 is preferably rigidly connected with first holder 14 and second holder 22 to form a first container comprising structure 103 that is rigid enough to withstand high centrifugal forces. It is not necessary, but preferred, that first container 10, first holder 14 and second holder 22 are made of one piece for stability and for manufacturing reasons. Further, first container 10 may be a hermetically closed container, with the exception of the opening provided by first holder 14. This would provide for a particular stable structure and protect the surroundings from spilled waste fluid. However, as it has turned out, it is not necessary for most processes to have a hermetically closed container. Further, manufacturing of the fluid processing device in one piece is less expensive if the first container is open in the top region. Furthermore, it may be necessary to have access to the waste fluid for control purposes.

Figure 3D:
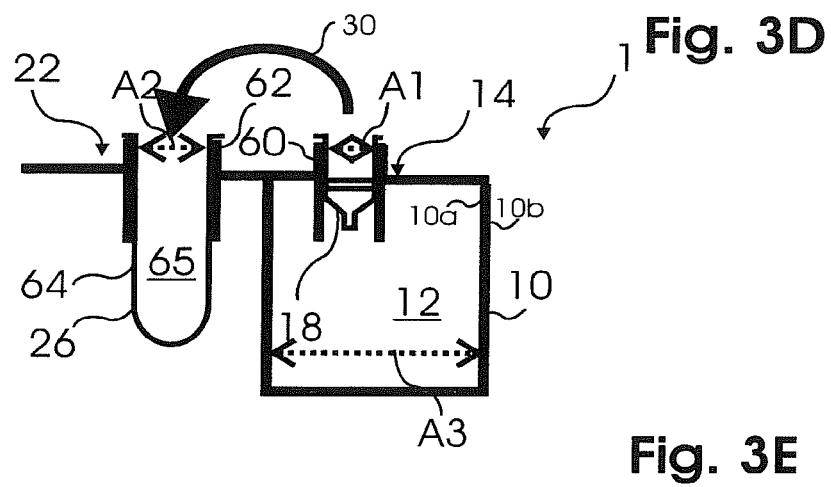
Figure 3E:
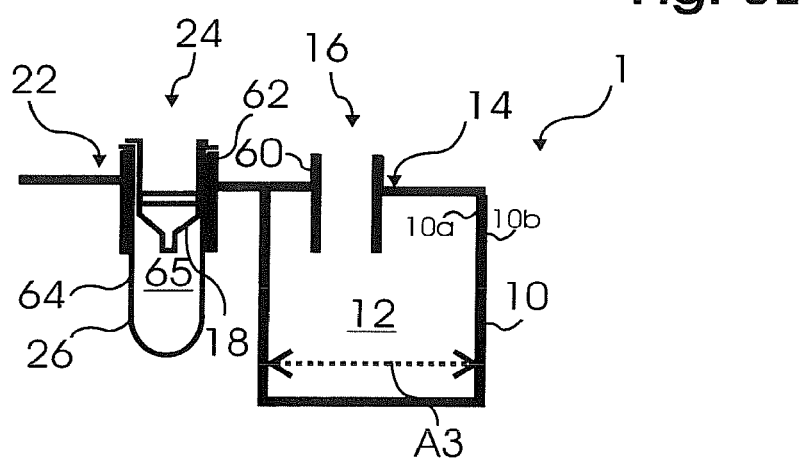

FIGS. 3D-3E illustrate, like FIGS. 2D-3E, a direct first tube transfer 30 of first tube 18 from first holding position 16 to second holding position 24. Again, with the fluid processing device of FIGS. 3A-3E, the elution step can be made to follow the binding and washing steps by applying a direct transfer 30 with three first tube movements: (a) sliding first tube 18 out of first holder 14; (b) moving first tube 18 from first holding position 16 to second holding position 24; and (c) sliding first tube 18 into second tube 26. However, different from FIGS. 2A-2E, there is first container 10 that can receive filtered fluids (lysate or wash fluids), i.e. waste fluid, that has left first tube 18 through its filter element 19. This way, waste fluid can be discarded in a way that it does not contaminate other tubes or fluids. Further, discarding is carried out without having to unload or reload the first tubes out of or into the centrifuge.

Figure 4C:
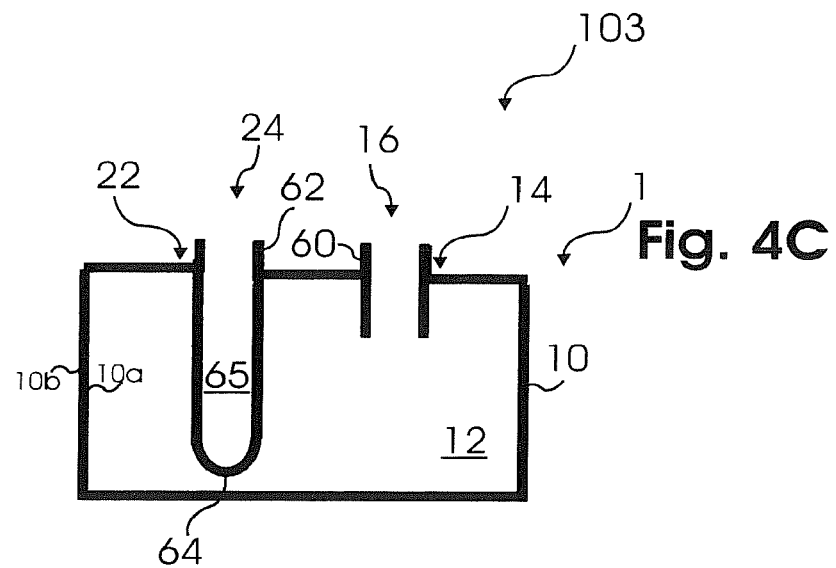

FIGS. 4A-4E disclose schematically a third fluid processing device according to the invention. FIG. 4A shows a cross sectional side-view along axis C1-C1' of the fluid processing device 1 holding a first tube 18 and a second tube 26 of the types as shown in FIGS. 1A and 1C. FIG. 4B shows a corresponding cross section along axis C1-C1' in a direction orthogonal to the side view of FIG. 4A. The fluid processing device 1 of FIGS. 4A-4E is the same as shown in FIGS. 3A-3E with the difference that first container 10 is extended to overlap second holder 22 in a projection orthogonal to first axis 11 of first tube 18 when held by first holder 14. This way, inner surface 10a of first container 10 adjoins to second holder 22. The design helps to significantly increase first container volume 12 to allow for more waste without having to increase the height of the container. Increasing the height of the first container would require the use of larger centrifuges. Further, with the shown extension of first container 10 to second holder 22, second holder 22 is connected more rigidly to first holder 14 to minimize deformation of fluid processing device 1 during centrifugation.

Fluid processing device 1 of FIGS. 4A-4E differs further from the embodiments of FIGS. 2a-2E and 3A-3E in that second holder 22 is form-fit to first tube 18 having a first cross section A1, instead of holding a second tube 26 having a second cross section A2. This way, the cylindrically-shaped inner faces of first holder 14 and the one of second holder 22 have the same axial cross sections. Further, different from the previous designs, second holder 22 extends into first container 10 to form a second container 64 having a second container volume 65. This way, for carrying out the binding, washing and elution steps, no second tube 26 is required since the purified biomolecules can be eluted into second container 64. However, since in this case second container 64 is rigidly connected with first holder 22 and first container 10, fluid processing device 1 has to be taken out of the centrifuge for further processing of the purified biomolecules. Furthermore, this embodiment is not suitable if storage of the purified biomolecules is desired.

Figure 4D:
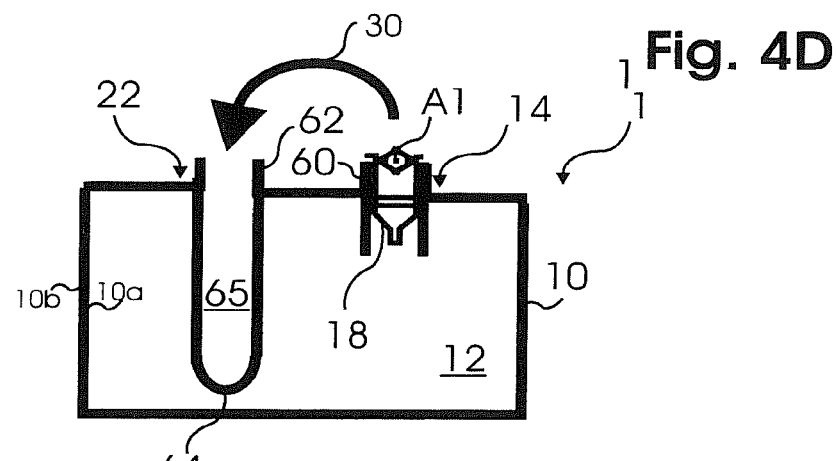
Figure 4E:
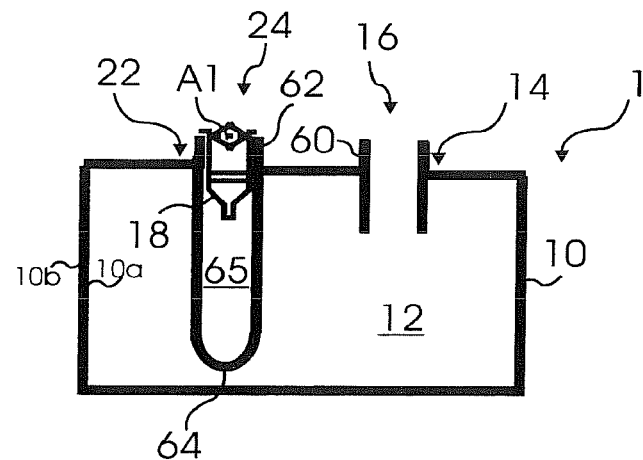

FIG. 4C illustrates a side view of fluid processing device 1 of FIG. 4A with the first tube removed. Again, preferably, the fluid processing device 1 as shown in FIG. 4C is made of one piece (first container comprising structure 103) in order to improve rigidity of the device and to reduce costs. Further, FIGS. 4D-4E illustrate, like FIGS. 3D-3E, a direct transfer 30 (first tube transfer) of first tube 18 from first holding position 16 to second holding position 24.

Figure 5A:
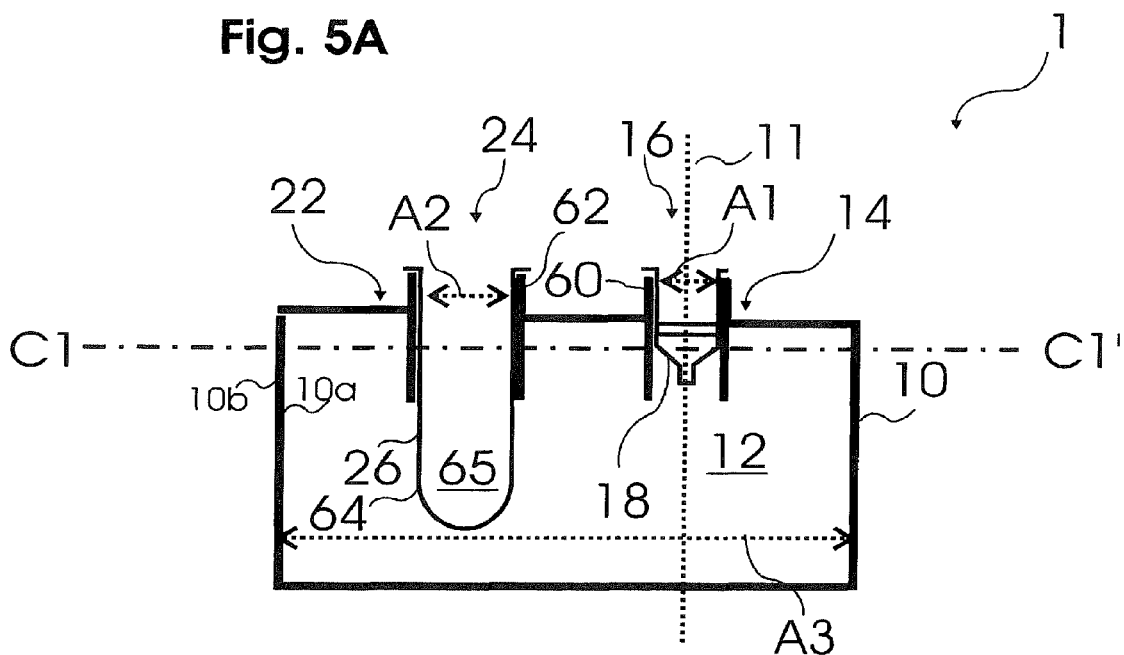
FIGS. 5A-5E: A fourth fluid processing device according to the invention for holding a first tube and a second tube having different cross sections whereby the fluid processing device has a first container extending beyond the second holder in a projection normal to the first axis.
Figure 5B:
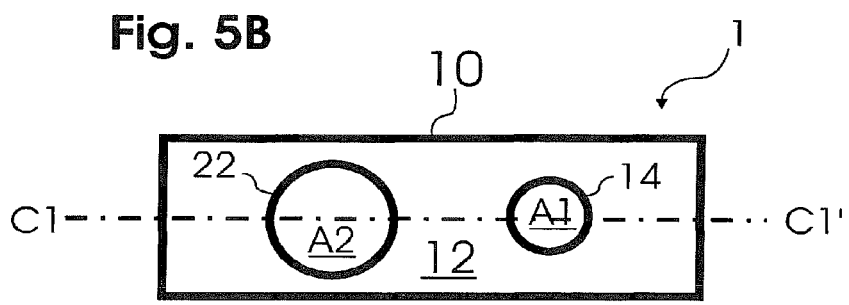

FIGS. 5A-5E disclose schematically a fourth fluid processing device according to the invention. FIG. 5A shows a cross sectional side-view along axis C1-C1' of the fluid processing device 1 holding a first tube 18 and a second tube 26 of the types as shown in FIGS. 1A and 1C. FIG. 5B shows a corresponding cross section along axis C1-C1' in a direction orthogonal to the side view of FIG. 5A. The fluid processing device 1 of FIGS. 5A-5E is the same as shown in FIGS. 4A-4E with the difference that second holder 22 is not extended to form a second container. Instead, for providing a second container 64 for elution, a second tube 26 needs to be inserted into second holder 22. Accordingly, in order to advance from the binding and washing steps to the elution step, first tube 18 has to be transferred from first holder 14 to second holder 22 and be slid into second tube 26 as disclosed in FIG. 1E. In this case, second tube 26 holds first tube 18 and, at the same time, serves as a second container for holding the elution fluid flowing through first tube 18. Further, since second tube 26 can be removed from fluid processing device 1, the eluted fluid with the eluted biomolecules can be removed from fluid processing device 1 for further processing or storage purposes without having the fluid processing device 1 to remove from the centrifuge.

Figure 5C:
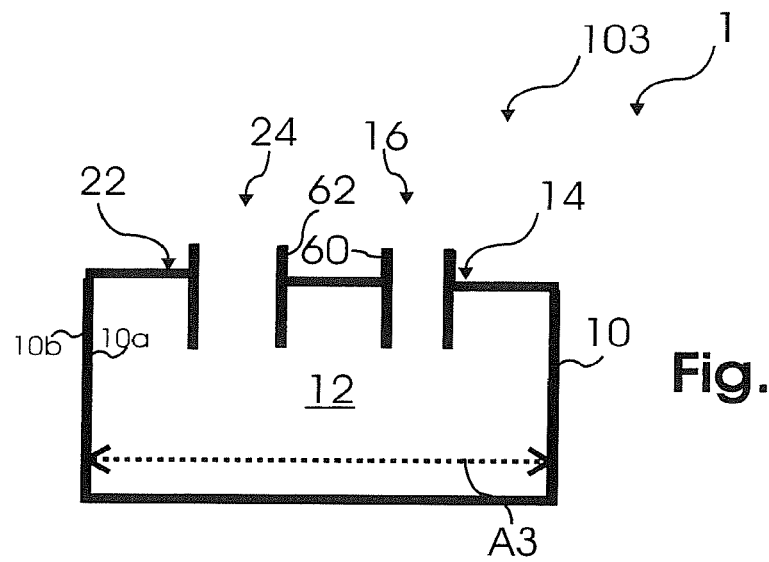
Figure 5D:
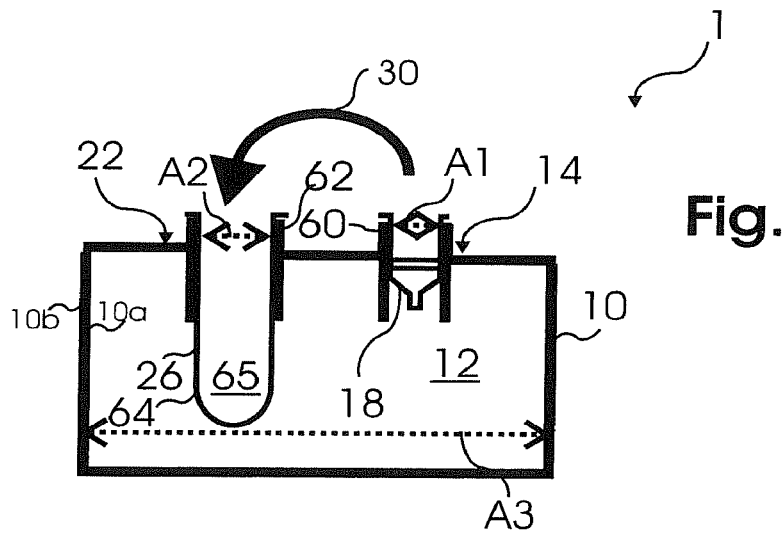
Figure 5E:
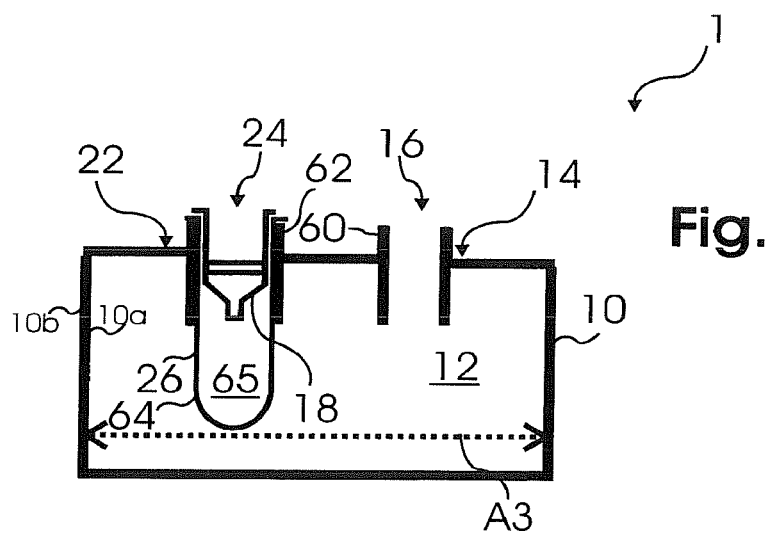

FIG. 5C illustrates a side view of fluid processing device 1 of FIG. 5A with first tube 18 and second tube 26 removed. Again, preferably, the fluid processing device 1 as shown in FIG. 5C is made of one piece (first container comprising structure 103) in order to improve rigidity of the device and to reduce costs. Further, FIGS. 5D-5E illustrate, like FIGS. 4D-4E, a direct transfer 30 (first tube transfer) of first tube 18 from first holding position 16 to second holding position 24.

Figure 6C:
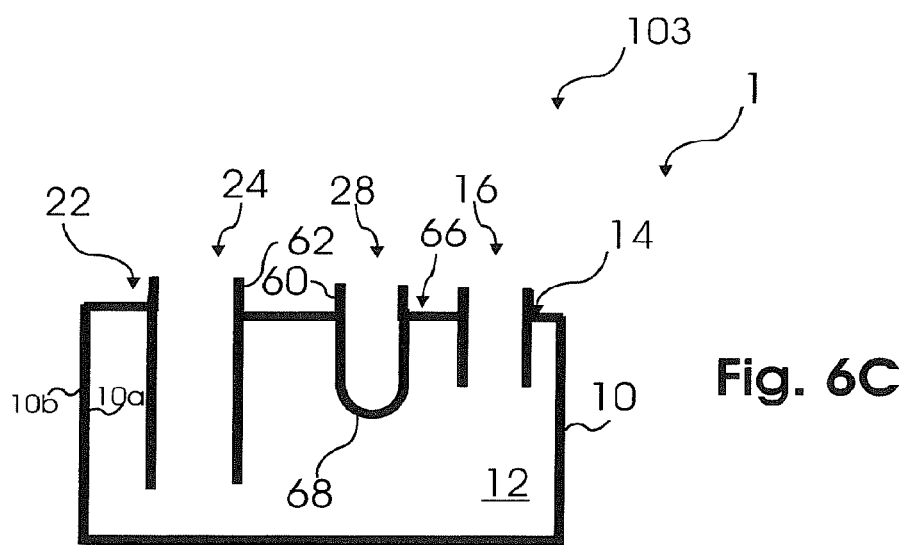

FIGS. 6A-6E disclose schematically a fifth fluid processing device according to the invention. FIG. 6A shows a cross sectional side-view along axis C1-C1' of the fluid processing device 1 holding a first tube 18 at a first holding position 16 and a second tube 26 at a second holding position 24. FIG. 6B shows a corresponding cross section along axis C1-C1' in a direction orthogonal to the side view of FIG. 6A. The fluid processing device 1 of FIGS. 6A-6E is the same as shown in FIGS. 5A-5E with the difference that a third holder 66 has been added for holding a third tube 32 having a third axis 34, a third cross section A3 and a third collar 33 at the tube's rim.

In FIG. 6A, third tube 32 is a further spin column having a third inlet opening, a third outlet opening and a filter element. In many applications, the geometry of the third tube 32 equals the geometry of the first tube 18 so that the third cross section A3 is the same as the first cross section A1. However, depending on the application, first tube 18 and third tube 32 may differ by their filter element type. Note that, if the first cross section A1 and the third cross section A3 are the same, the inner face of first holder 14 may be the same as the inner face of third holder 66 so that the first tube 18 may also be held by third holder 66 and the third tube 32 may be also held by the first holder 14 if required by the process.

Further, third holder 66 is extended to provide for a third container 68 having a third container volume 70. Further, depending on the application, third holder can be made to hold a first tube 18 having a first cross section A1 or to hold a second tube 26 having a second cross section A2. As can be seen from the figures, third holder 66 has a cylinder-like shaped inner face that is form-fit to the shape of third tube 32. This way, by sliding third tube 32 into the inner cylinder-like shaped face, third tube's 32 position is defined within a plane orthogonal to the sliding direction. Further, the upper rim of the cylinder-like shaped face of third holder 32 is such that it functions as a third stopper 67 that stops the sliding of third tube 32 into third holder 66 at the moment when third collar 33 hits stopper 67. In this position, third tube's 32 position is also defined in sliding direction as long as gravitational or centrifugal forces have a component pressing third collar 33 onto third stopper 67. Again, it is preferred that third holder 66 is arranged such that it holds third tube 32 such that third tube 32 is in parallel to first tube 18 when held by first holder 14.

Third holder 66 is useful for implementing additional purification steps into the fluid processing device 1. For example, some applications require additional filter elements with different functionalities. Third holder 66 can be used for holding a third tube 32 with a filter element differing in its specificity or functionality from the filter element of first tube 18. Third tube 32 is arranged in a way that a fluid containing the desired biomolecules flows through third tube 32 into third container 70 when held by third holder 66 in third holding position 28. Before gaining access to the fluid containing the desired biomolecules the third tube 32 has to be removed from the third holder 66.

Further, third holder 66 can be used without another filter element for lysate clearing after lysis of an initial biological sample before performing the binding, washing and elution steps. Lysing of the biological sample may be carried out separately, for example, by dispensing a lysing buffer to the sample fluid in order to break up the cell walls of the cells containing biomolecules, e.g. nucleic acids. After addition of a further buffer, for example a neutralization buffer, the lysat is transferred into the third container volume 70 of third container 68. In order to pellet the cell debris in third container 68 centrifugal force is applied to the fluid processing device 1, and the supernatant containing biomolecules, i.e. the cleared nucleic acid containing fluid, is pipetted from third container 68 into first tube 18 to initiate the binding step.

Note that the above method would also work with a third tube 32 if third tube 32 is formed as a container and placed in the third holding position 28. In this case the initial biological sample is dispensed into the third tube 32 after lysis.

Also note that, as can be seen from FIGS. 6A-B, first container 10 is extended in a projection orthogonal to first axis 11 of first tube 18 held by first holder 14 in a way that it covers second holder 22 and third holder 66. Again, this is to maximize the first container volume 12 at a given container height in order to maximize the waste volume.

Figure 6D:
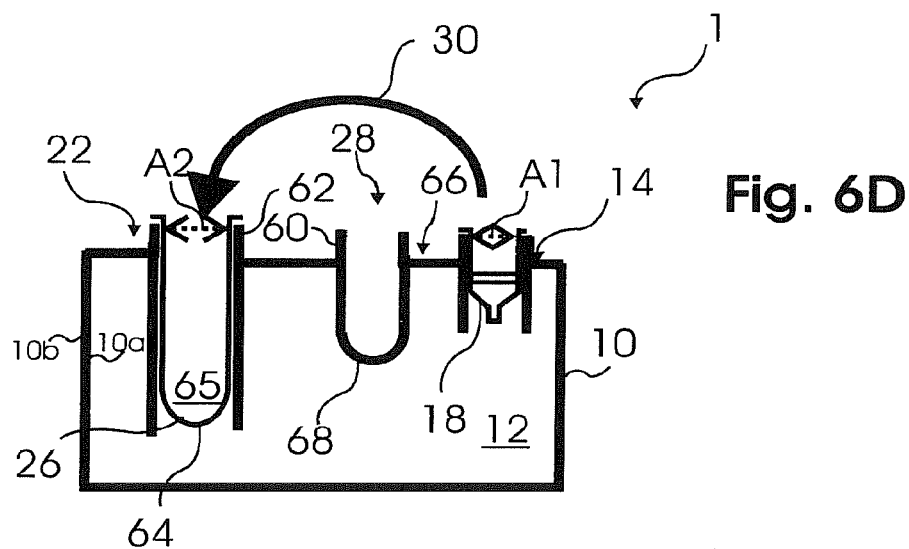
Figure 6E:
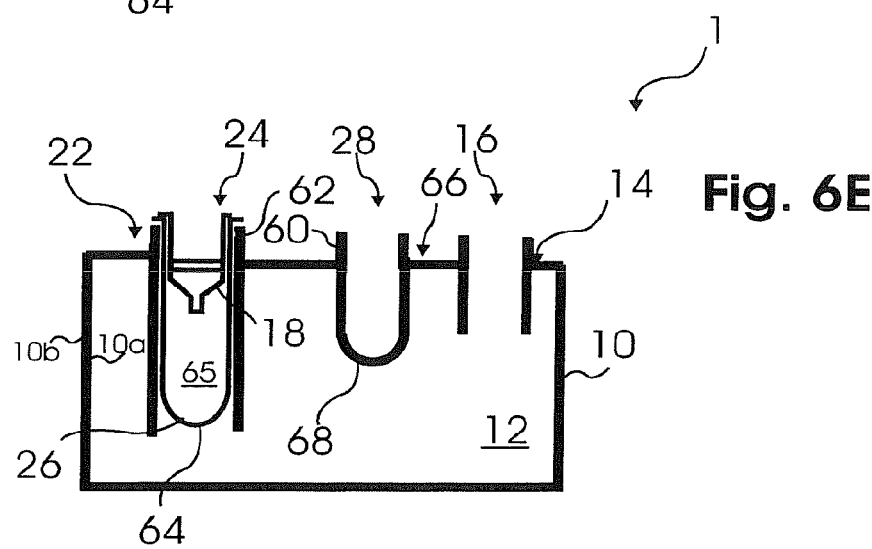

FIG. 6C illustrates again a side view of fluid processing device 1 of FIG. 6A with first tube 18, second tube 26 and third tube 32 removed. Again, preferably, the fluid processing device 1 as shown in FIG. 6C is made of one piece (first container comprising structure 103) in order to improve rigidity of the device and to reduce costs. Further, FIGS. 6D-6E illustrate, like FIGS. 5D-5E, a direct transfer 30 (first tube transfer) of first tube 18 from first holding position 16 to second holding position 24 for the elution step.

Figure 7A:
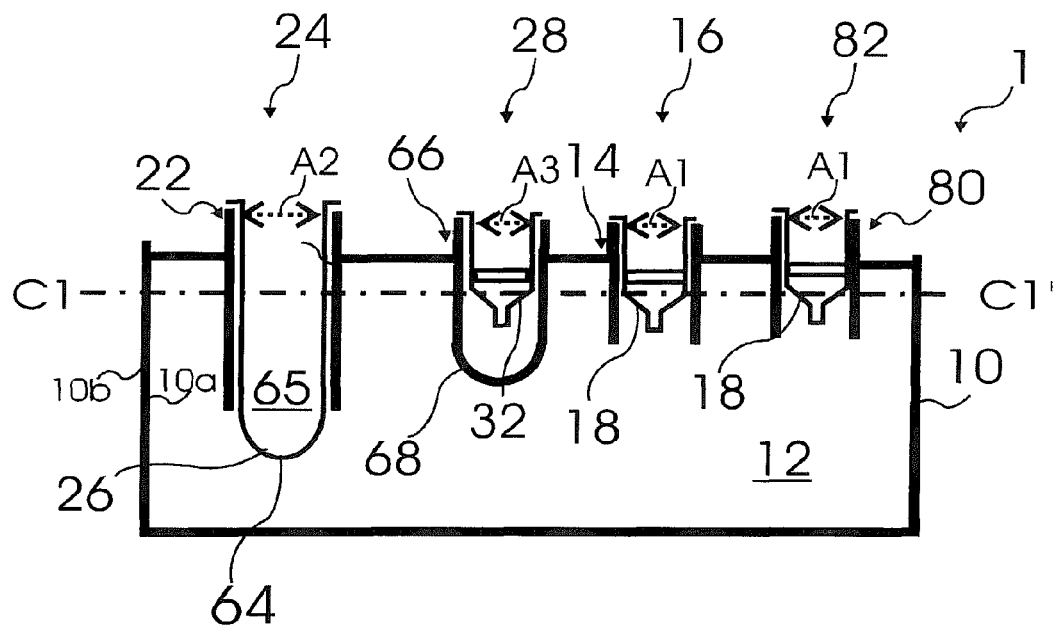
FIGS. 7A-7B: A sixth fluid processing device according to the invention for holding a first tube, a second tube, a third tube and a fourth tube having different cross sections whereby the fluid processing device has a first container.
Figure 7B:
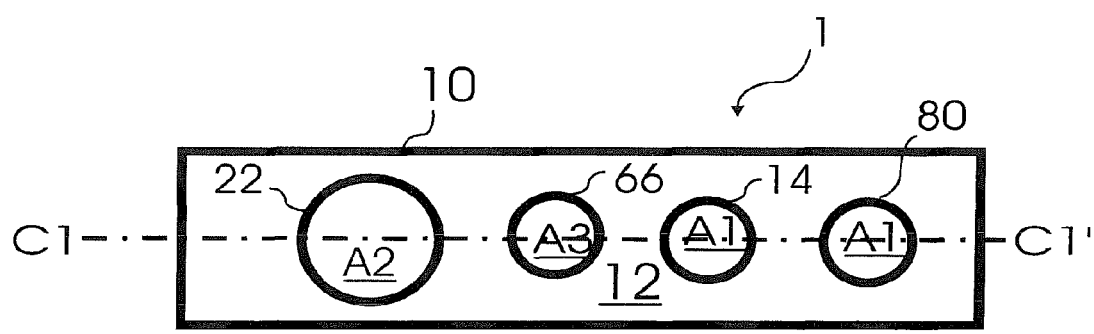

FIG. 7A-7B illustrates two orthogonal cross sections through a sixth fluid processing device 1 according to the invention. The fluid processing device 1 of FIG. 7A-7B is the same as the one of FIGS. 6A-6F except that it contains a fourth holder 80 for holding a further first tube 18. The further first tube 18 is held by holder 80 such that a fluid flowing through further first tube 18 holder also flows into first container 10. With the first holder 14 holding a first tube 18 and fourth holder 80 holding a further first tube 18, it is possible to bind and wash two different biomolecules at a time.

Figure 8A:
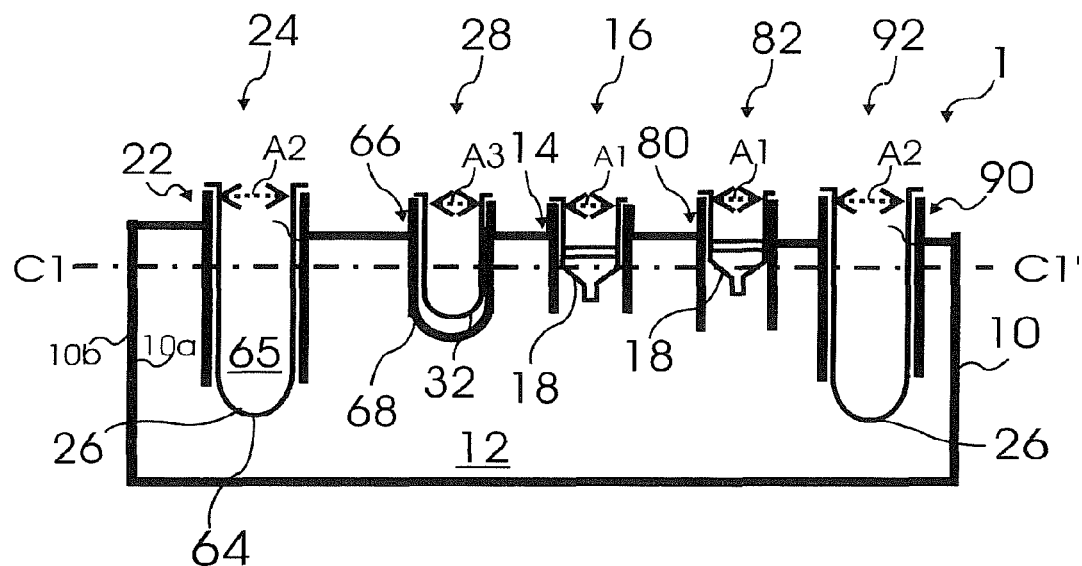
FIGS. 8A-8B: A seventh fluid processing device according to the invention for holding a first tube, a second tube, a third tube, a fourth tube and a fifth tube having different cross sections whereby the fluid processing device has a first container.
Figure 8B:
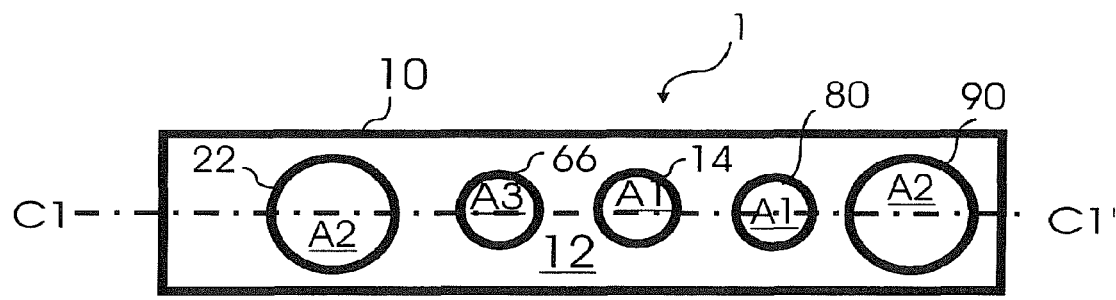

FIGS. 8A-8B illustrate two orthogonal cross sections through a seventh fluid processing device 1 according to the invention. Fluid processing device 1 of FIGS. 8A-8B is identical the embodiment of FIGS. 7A-7E with the exception that it includes a fifth holder 90 holding a further second tube 26. This embodiment is to show that the present invention allows including at least five holders, e.g. two holders for holding a first tube 18, two holders for holding a second tube 26 and one tube for holding a third tube 32. Depending on a process sequence and on the size of the centrifuge to be used, if multiple holders are required to simplify the process sequence, the present invention enables the provision of the required multiple holders of different sizes. Also, while in the figures of the description the various holders are linearly aligned along axis C1-C1', it is also possible to arrange holders distributed within two dimensions, e.g. within two lines or as an arbitrary array.

The fluid processing devices described so far do not include connection means. However, as mentioned before, with connection means that have a holding structure for holding the fluid processing device 1, it is possible to connect those fluid processing devices to the rotor, as a skilled person will know.

Figure 9A:
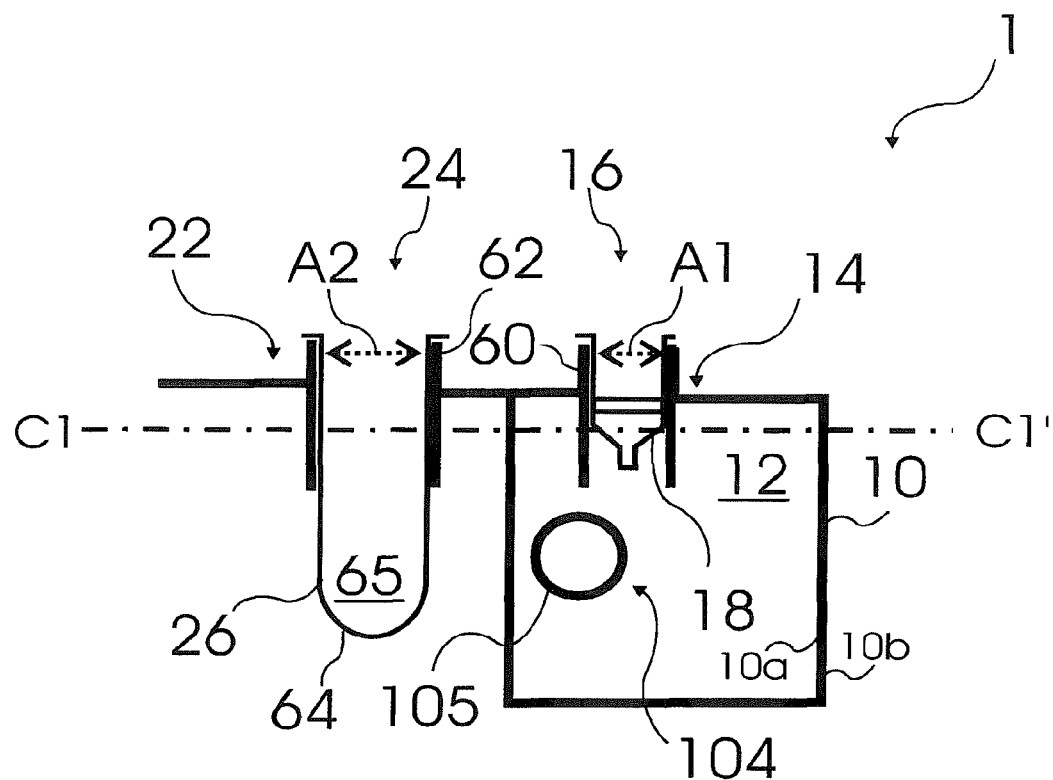
FIGS. 9A-9B: An eighths fluid processing device according to the invention for holding a first tube and a second tube having different cross sections, the fluid processing device having a first container and having connection means.

FIGS. 9A-8B illustrate two orthogonal cross sections through an eighths fluid processing device 1 according to the invention. The eighths fluid processing device is identical to the embodiment of FIGS. 3A and 3B with the difference that the present embodiment comprises connection means 104 for connecting fluid processing device 1 to a rotor of a centrifuge. In the present case, connection means 104 consist of two swing axle elements 105 that are integrally connected with two opposing sides of first container 10. The two swing axle elements 105 are shaped like two frusta pointing outwardly with respect to first container 10 to define swing axis 106 that extends through first container volume 12. As will be shown later in more detail, in order to removably connect fluid processing device 1 to a rotor of a centrifuge, the two frusta-shaped swing axle elements 105 are hung into respective receiving rotor connection means 134, e.g. swing axle receivers 128, that are part of two opposing arms of the rotor.

Figure 9B:
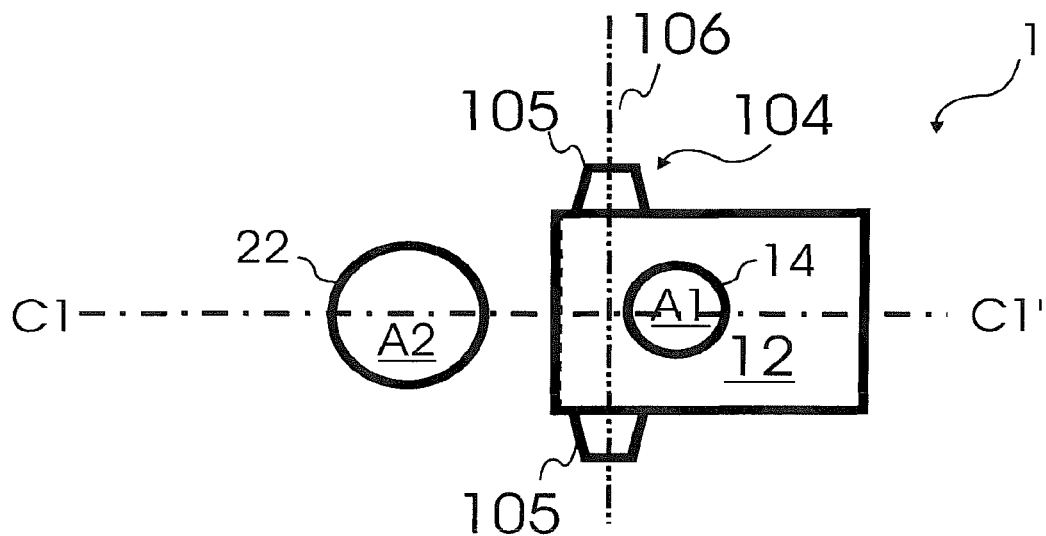

Swing axle elements 105 of fluid processing device 1 and receiving rotor connection means 134, e.g. swing axle receivers 128, of the rotor are positioned and adapted with respect to each other such that fluid processing device 1 can turn around a swinging axis 106 that extends in tangential direction with respect to the rotation of the rotor in the centrifuge. This way, one or more of the fluid processing devices 1 of FIGS. 9A-9B can be centrifuged in a way that the fluid processing devices are free to swing outwardly around swinging axis 106 depending on the centrifugal force. This way, if the centrifugal force is very high compared to the gravitational force, the fluid processing devices may swing so far outwardly that the tubes have an almost horizontal orientation. In this case, the fluids within the first and second tubes are pressed under centrifugal force in almost axial direction towards the tube's floor or through the tube's filter element. Generally, it is preferred that swing axle elements 105, e.g. two frusta or cylinders, are integrally connected with first container 10, first holder 14 and second holder 22. If this is the case, the fluid processing device 1 is said to be self-supported. In a preferred embodiment, however, the fluid processing device 1 is not self-supported. In this case, it is preferred that the connection means 104 have a holding structure 102 that is adapted for holding the fluid processing device 1 during centrifugation as shown, for example, in FIG. 12.

It should be mentioned that the use of cylindrically or frusta-shaped swing axle elements 105 is only one of many ways to implement a swinging fluid processing device 1 to a rotor of a centrifuge. For example, instead of swing axle elements 105 pointing outwardly with respect to first container 10, two recesses at the respective sides of first container 10 can be used that are shaped to engage with the receiving rotor connection means 134, e.g. swing axle receivers 128, of the rotor such that fluid processing device 1 can swing outwardly under centrifugal force. Further, it is also possible to place swing axle elements 105 in such a way with respect to first container 10 that they define a swinging axis 106 that runs outside of first container volume 12. In this case, the connection means 104 may use a hinge joint that is biased by a spring for making a swinging connection with the rotor, instead of using a frusta-shaped swing axle element.

Figure 10A:
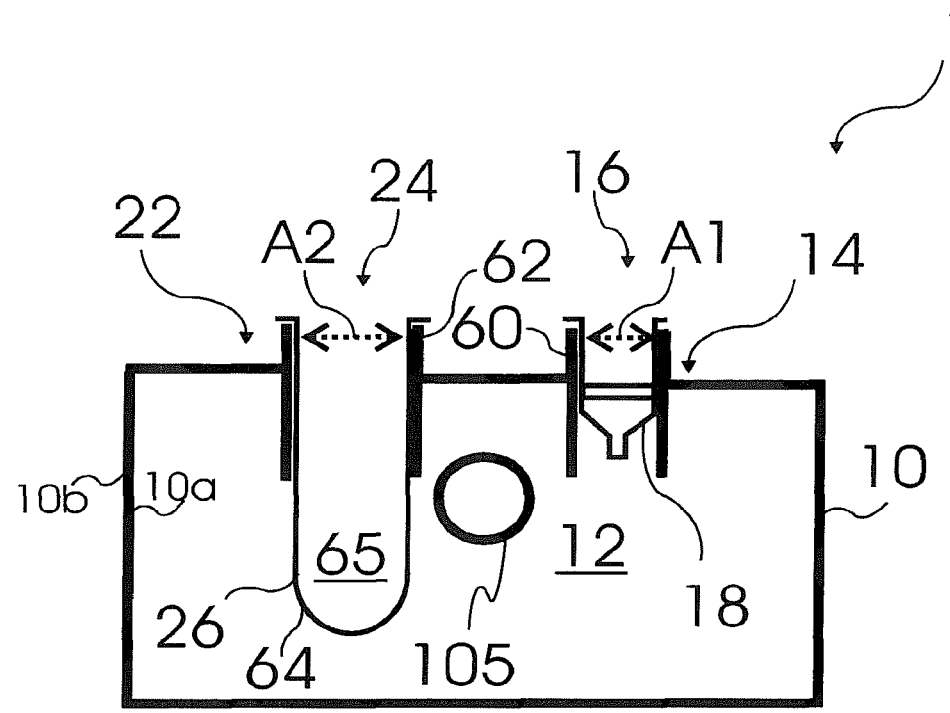
FIGS. 10A-10B: A ninth fluid processing device according to the invention for holding a first tube and a second tube having different cross sections whereby the fluid processing device has a first container extending beyond the second holder in a projection normal to the first axis and, further, having connection means.
Figure 10B:
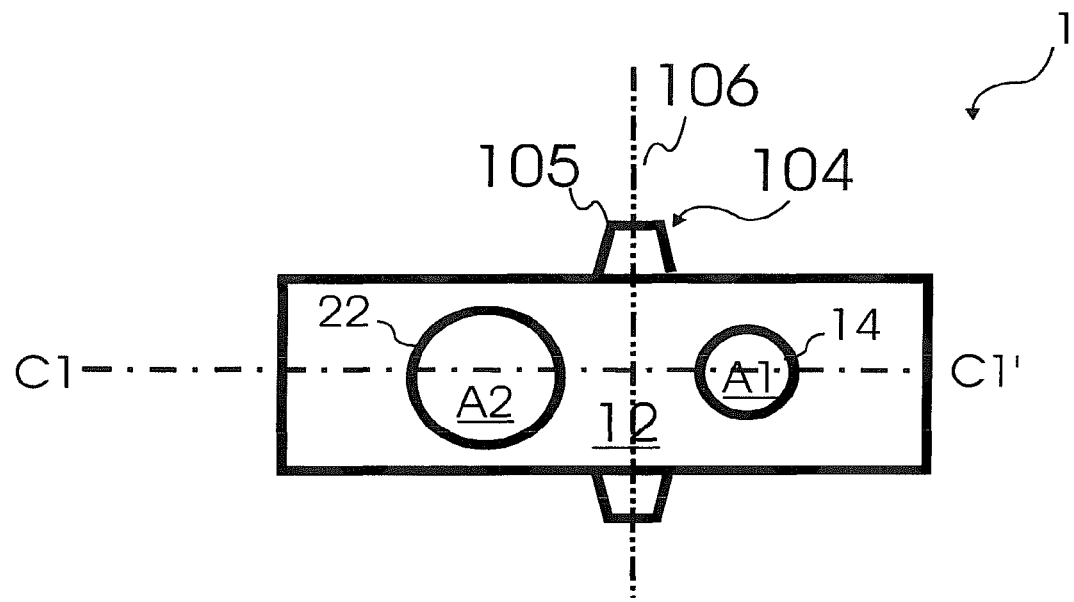

FIGS. 10A-10B illustrate two orthogonal cross sections through a ninth fluid processing device 1 according to the invention. Fluid processing device 1 of FIGS. 10A-10B is identical to the embodiment of FIGS. 4A-4E with the exception that, like in FIGS. 9A-9B, the fluid processing device 1 is self-supported because of the integrally connected two frusta 105 for connecting fluid processing device 1 with a rotor of a centrifuge.

Figure 11A:
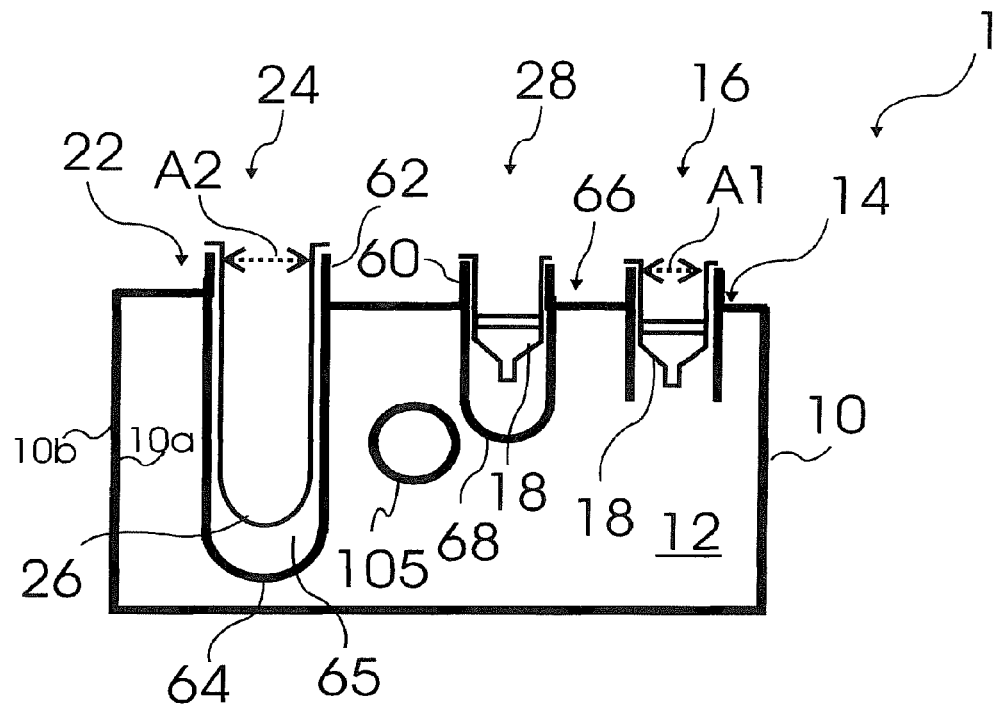
FIGS. 11A-11B: A tenth fluid processing device according to the invention for holding a first tube, a second tube and a third tube having different cross sections whereby the fluid processing device has a first container and, further, connection means.
Figure 11B:
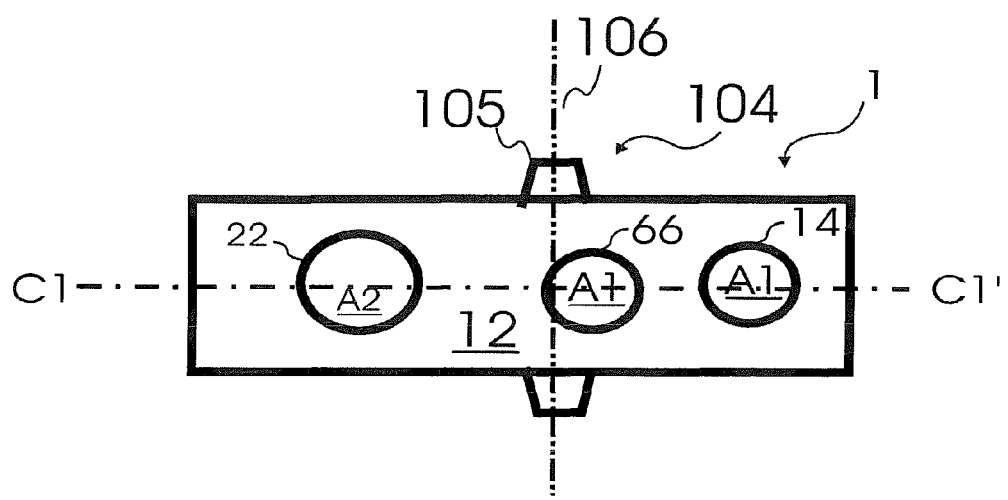

FIGS. 11A-11B illustrate two orthogonal cross sections through a tenth fluid processing device 1 according to the invention. Fluid processing device 1 of FIGS. 11A-11B is similar to the embodiment of FIGS. 6A-6E with the exception that, like in FIGS. 10A-10B, the fluid processing device 1 is self-supported because of its integrally two frusta 105 for connecting fluid processing device 1 with a rotor of a centrifuge.

Figure 12:
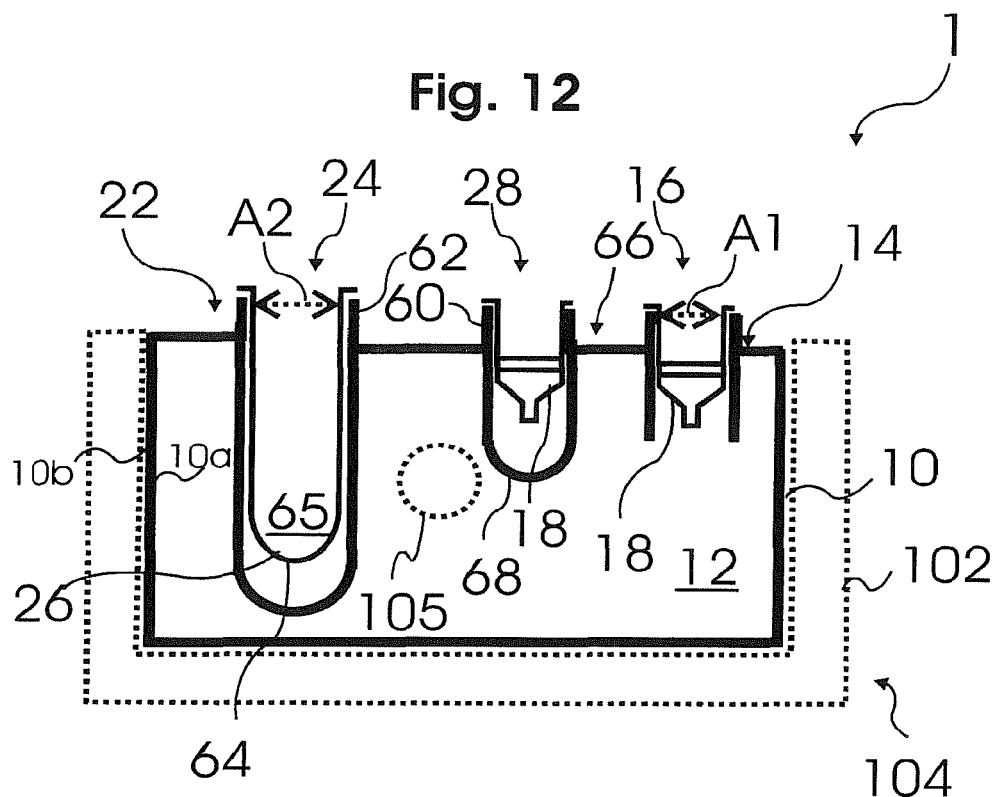
FIG. 12: An eleventh fluid processing device according to the invention for holding a first tube, a second tube and a third tube having different cross sections whereby the fluid processing device has a first container and connection means comprising a holding structure for removably holding the first container.

FIG. 12 discloses an eleventh fluid processing device according to the invention that is identical to the embodiment according to FIGS. 11A-11B except that connection means 104 comprise in addition to swing axle elements 105 a holding structure 102 for holding first container 10 with first holder 14, second holder 22 and third holder 66. In this case, connection means 104 and the structure comprising first container 10 can be considered as separate units that are adapted to each other to be removable connectable with each other. Further, in FIG. 12, the inner face of holding structure 102 is form-fit to the outer face 10b of first container 10 to make sure that holding structure 102 and first container comprising structure 103 are in a defined position with respect to each other, at rest as well as during centrifugation.

On the other hand, for simplifying handling, it is preferred that holding structure 102 has an opening large enough so that first container comprising structure 103 can be removed from holding structure 102 by simply extracting first container comprising structure 103 from holding structure 102. For example, in FIG. 12, holding structure 102 is cup-shaped with the inner face of the cup form-fit to the outer shape of first container 10. This way, first container comprising structure 103 consisting of first container 10, first holder 14, second holder 22, and third holder 66 can be separated from cup-shaped holding structure 102 by extracting the two from each other.

In a preferred embodiment, first container comprising structure 103 and holding structure 102 are shaped such that first container comprising structure 103 can be inserted into holding structure 102 at only one orientation with respect to each other. This is to prevent that, e.g., a user confuses first and second tubes by inserting the container comprising structures into holding structures accidentally at different orientations.

In a further preferred embodiment, first container comprising structure 103 and holding structure 102 are shaped such that it is possible to insert first container comprising structure 103 into holding structure 102 at two different orientations, preferably at an angle of 180 degrees between the two orientations. The two orientations can be used to allow the connection means 104 to be connected with the rotor of the centrifuge in two opposite directions. This in turn makes it possible that the fluid processing devices in the rotor can be centrifuged at two different predetermined swinging angles αs (see FIG. 18C), depending on the chosen orientation. The predetermined swinging angle as indicates the maximum angle at which the fluid processing devices swing within the rotor arms 126, with respect to the orientation at rest.

It should be noted that it is preferred that connection means 104 comprising holding structure 102 and swing axle elements 105 are made of one piece. Further, in order to withstand the centrifugal force exerted to first container comprising structure 103, it is preferred that holding structure 102 is made of a material that is light but has a high strength, e.g. aluminum. Also, if the first container comprising structure 103 is removable from holding structure 102, it may be an option that swing axle elements 105 and receiving rotor connection means 134, e.g. swing axle receiver 128, are adapted to provide for a permanent connection.

Figure 13:
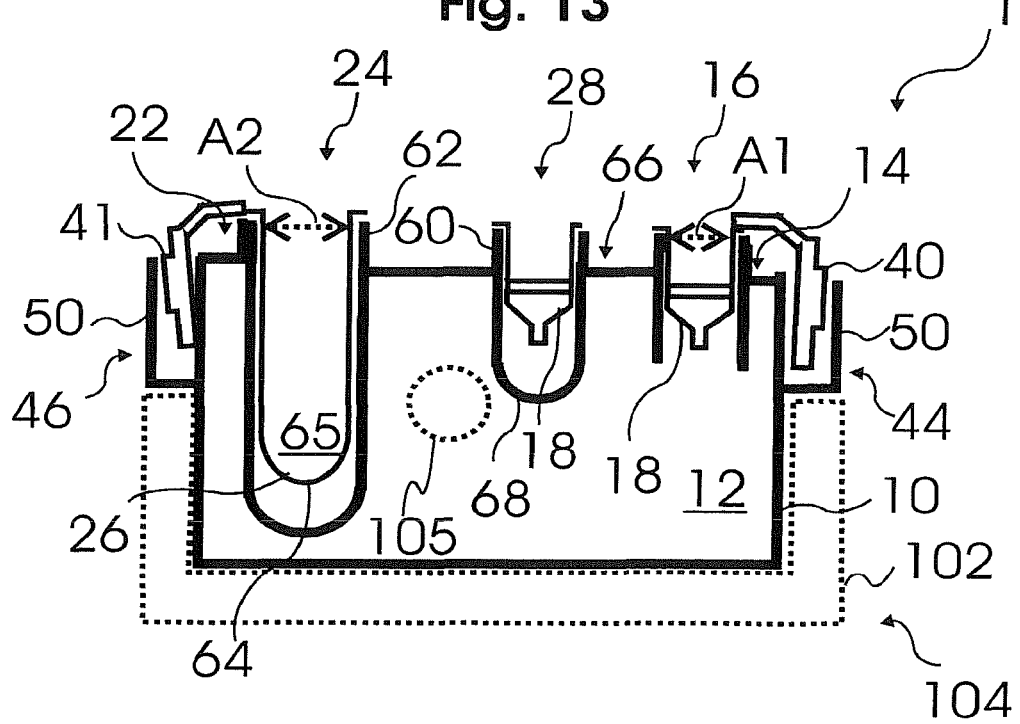
FIG. 13: An twelfth fluid processing device according to the invention that is like the eleventh fluid processing device including first and second cap fixture means for holding first and second caps.

FIG. 13 discloses a twelfth fluid processing device according to the invention that is identical to the embodiment according to FIG. 12 except that the present fluid processing device 1 includes first cap fixture means 44 for holding a first cap 40 of a first tube 18 during centrifugation and second cap fixture means 46 for holding a second cap 41 of a second tube 26 during centrifugation. With the first cap fixture means 44 and the second cap fixture means 46 it is possible to centrifuge tubes with an open inlet opening, i.e. centrifuging tubes that have a cap connected to it with their caps taken off. Centrifuging tubes with an open inlet opening is advantageous since, when automatically transferring first tube 18 from first holder onto second tube 26, no step for taking off second cap 41 from second tube 26 is required. Further, with an open first tube, it is not necessary to take off first cap 40 from first tube 18 in order to withdraw or dispense a fluid from or into the first tube 18. This significantly simplifies automation.

In FIG. 13, first cap fixture means 44 are realized by providing a cap enclosure structure 50 in which first cap 40 can be slid in at the same time as first tube 18 is slid into first holder 14. With first cap 40 slid into cap enclosure structure 50, first cap 40 does not have the freedom anymore to freely move during centrifugation. This is to avoid any damage that a freely moving cap that is flexibly connected to a tube could cause during centrifugation. Preferably, cap enclosure structure 50 is integrally connected with first holder 14. Of course, a skilled person will know what shape and size to choose for the cap enclosure structure 50 depending on the type of tube that is to be held.

Similarly, second cap fixture means 46 in FIG. 13 are realized by providing a cap enclosure structure 50 in which second cap 41 can be slid in at the same time as second tube 26 is slid into second holder 22. Like for first tube 18, with second tube 26 slid into cap enclosure structure 50, second cap 41 does not have the freedom anymore to freely move during centrifugation to cause any damage. Further, like for first tube 18, cap enclosure structure 50 of second cap fixture means 46 is preferably integrally connected with second holder 14. Preferably, the first and second cap fixture means are mounted to the inner or outer surface 10a, 10b of the first container 10.

Figure 14A:
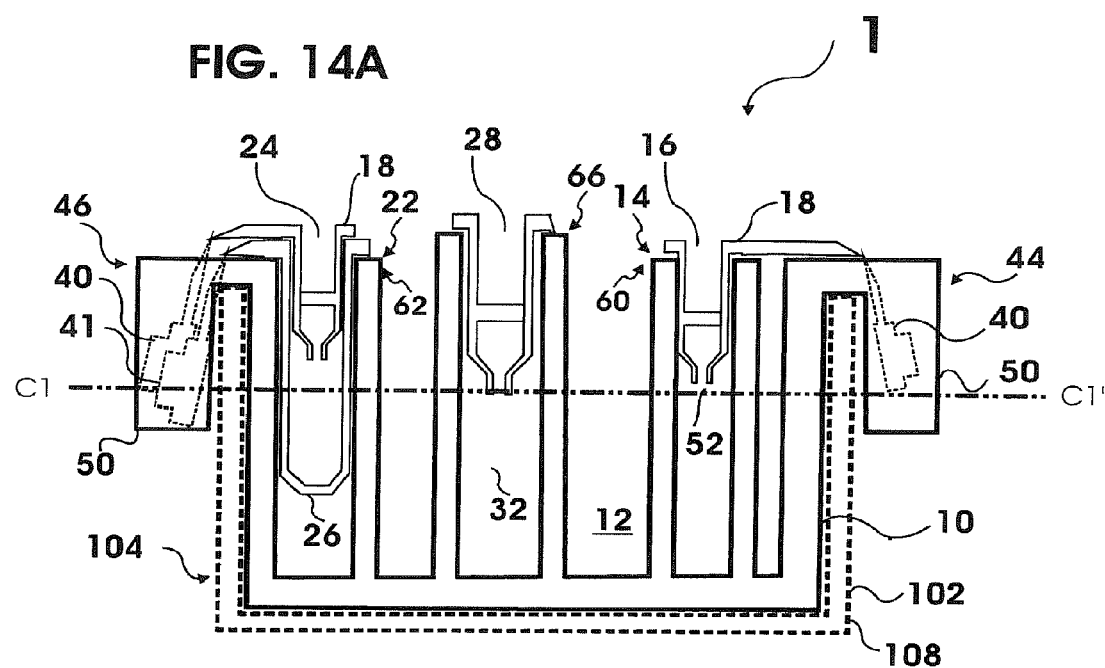
FIGS. 14A-14B: An thirteenth fluid processing device according to the invention that is like the twelfth fluid processing device including two first cap fixture means and one second cap fixture means.
Figure 14B:
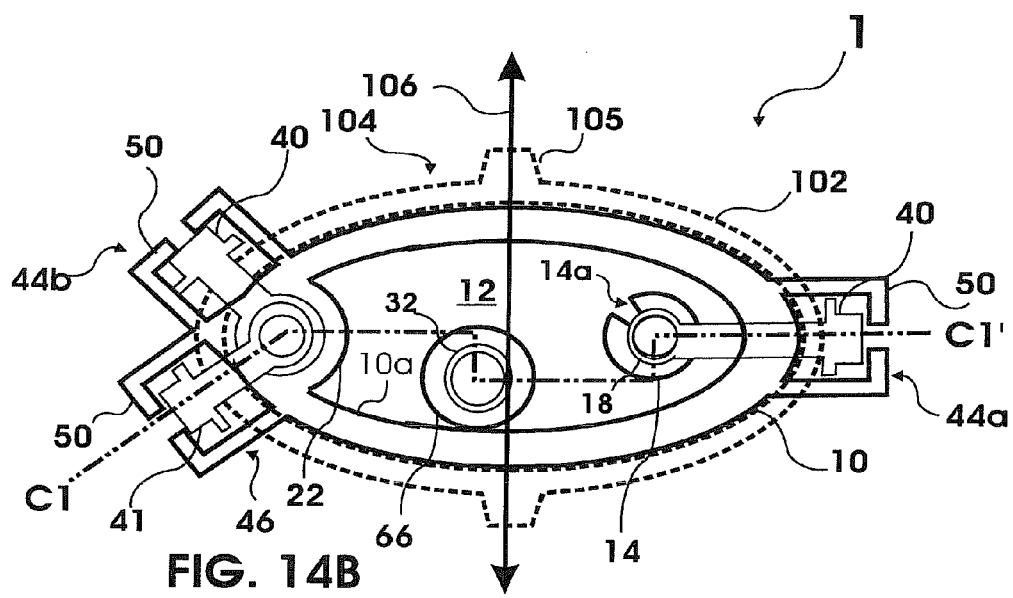

FIGS. 14A-14B disclose a further preferred embodiment according to the invention in two orthogonal cross sections that in many ways resembles the embodiment according to FIG. 13. However, different from FIG. 13, the embodiment of FIGS. 14A-14B comprises two first cap fixture means 44a, 44b of the kind as explained in FIG. 13. This way, it is possible to have first cap 40 of first tube 18 held by first cap fixture means 44 in the cases where first tube 18 is positioned in a first holding position 16 as well as in a second holding position 24. This way, it is possible to transfer first tube 18 with first cap 40 from first holder 14 for binding and washing steps to second holder 22 for an elution step without having to worry of any damage caused by a freely moving first cap during centrifugation. It should be noted that for spatial reasons, the orientation of first first cap fixture means 44a adjacent to first holder 14 is rotated by approximately 145 degrees with respect to the second first cap fixture means 44b adjacent to second holder 22. This implies that, in order to transfer first tube 18 from first holder 14 to second holder 22, it is necessary to rotate first tube 18 by approximately by 145 degrees for the second first cap fixture means 44b to hold first cap 40. As shown in FIG. 13, other rotating angles are possible as well.

The embodiment of FIGS. 14A-14B differs further from the embodiment of FIG. 13 in that the three holders, i.e. first holder 14, second holder 22 and third holder 66, have a cylindrical shape extending from the floor of first container 10 to the stopper planes defined by respective first, second and third stoppers 60, 62, 67 for holding respective tubes. Further, in this embodiment, the outer wall of the cylindrically shaped second holder 22, and the outer wall of cylindrically shaped third holder, are in direct contact with the inner wall 10a of first container 10. This arrangement provides for good strength against deformation due to centrifugal forces in the case that a large component of the centrifugal force acts in axial direction of the tubes. It should be noted that, in order to improve the rigidity of the fluid processing device 1 during centrifugation, it is generally preferred that more than one, or all, of the cylindrically shaped holders are positioned within first container 10 such that they are in direct contact with both the inner wall 10a and the floor of first container 10.

It is further to be noted that the cylinder jacket of first holder 14 is provided with a cylinder jacket slit 14a extending in parallel to the axis of the cylinder in order to provide for a fluid connection between first container volume 12 and the volume inside of cylinder jacket of first holder 14. This ensures that fluid leaving outlet opening 52 of first tube 18 at first holding position 16 flows outside of the cylinder into first container volume 12. For example, if a binding and washing step is carried out with first tube 18 at first holding position 16, the waste fluid is free to leave the cylinder of first holder 14 through cylinder jacket slit 14a into first container volume 12.

Figure 15:
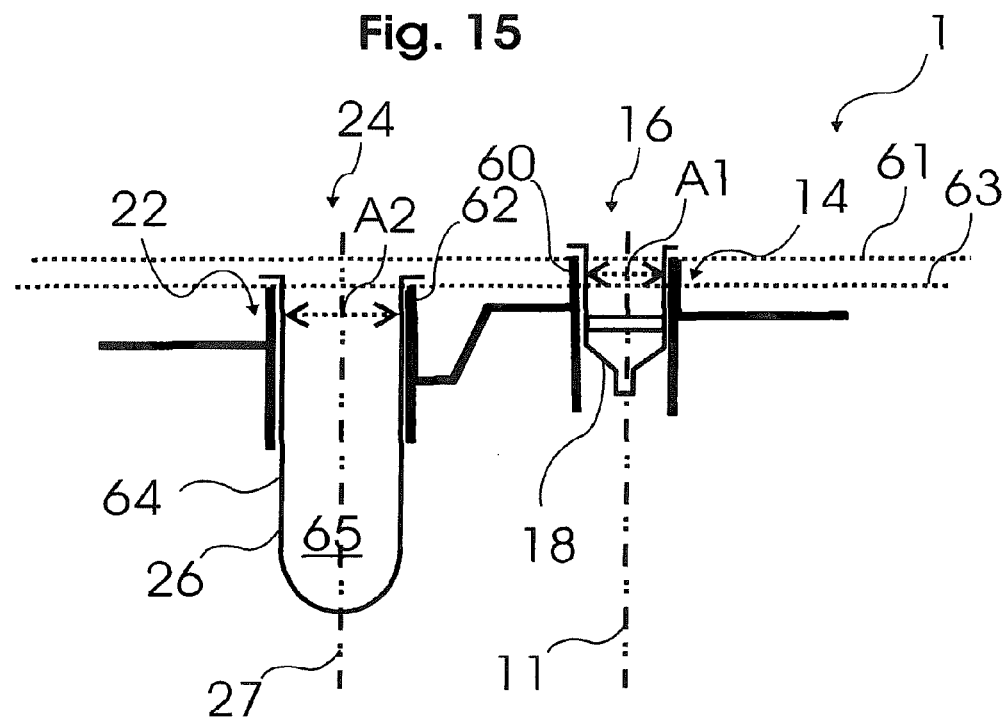
FIG. 15: A fourteenth fluid processing device according to the invention having a first stopper and a second stopper defining different stopper planes.

FIG. 15 discloses a further fluid processing device 1 according to the invention in which first stopper 60 of first holder 14 defines a first stopper plane 61 that is different from second stopper plane 63 defined by second stopper 62 of second holder 22. This way, it is possible to hold first tube 18 at a height different from the height of second tube 26 as measured along the projections onto respective first or second tube axes 11, 27. Holding first and the second tubes 18, 26 at different heights provides for an option of easier accessing the tubes for removing a tube from a holder or for placing a tube into a holder in the case that first holder 14 and second holder 22 are positioned very close to each other. Generally, it is preferred that the two stopper planes 61, 63 are in parallel with each other since in this case, it is easier to transfer a first tube 18 from a first holder 14 to a second holder 22 in an automated fashion.

Figure 16:
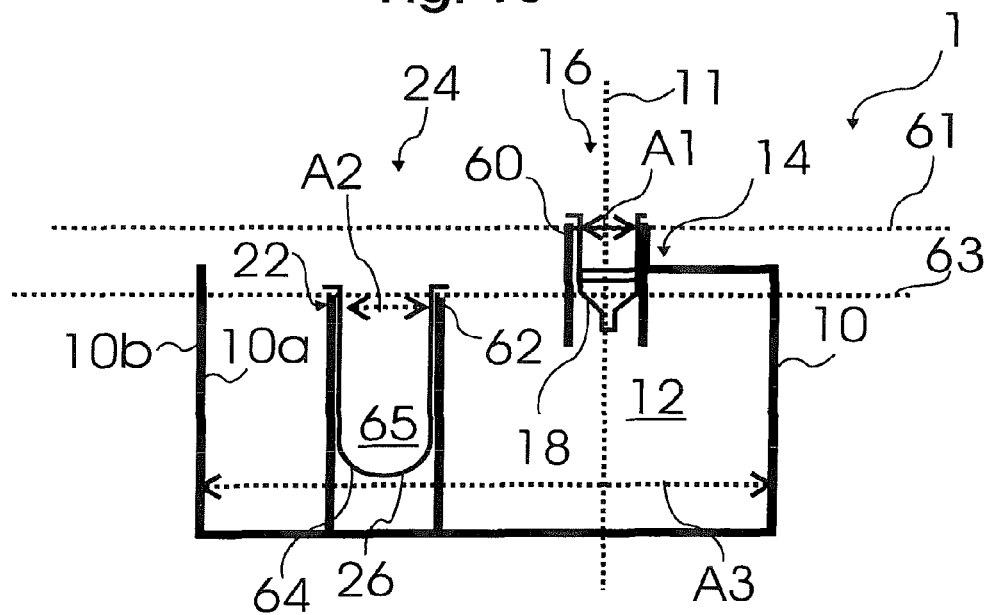
FIG. 16: A fifteenth fluid processing device according to the invention having a first container as well as a first stopper and a second stopper defining different stopper planes.

FIG. 16 discloses a further variation of a fluid processing device 1 according to the invention. Like in FIG. 15, fluid processing device 1 has first holder 14 for holding a first tube 18 and second holder 22 for holding a second tube 26 and respective first and second stoppers 60, 62 that define a first stopper plane 61 and a second stopper plane 63 that differ from each other. However, different from FIG. 15, fluid processing device 1 includes a first container 10 whereby first holder 14 is arranged with respect to first container 10 so that a fluid flowing through first tube 18 flows into first container 10. Further, first holder 14 is mounted to a wall of first container 10 while second holder 22 is mounted to the floor of first container 10. This way, inner surface 10a of first container 10 adjoins to first holder 14 and second holder 22. Although not explicitly shown in FIG. 16, it is generally preferred that the holders are in rigid contact with the side walls and the bottom of the container.

Figure 17A:
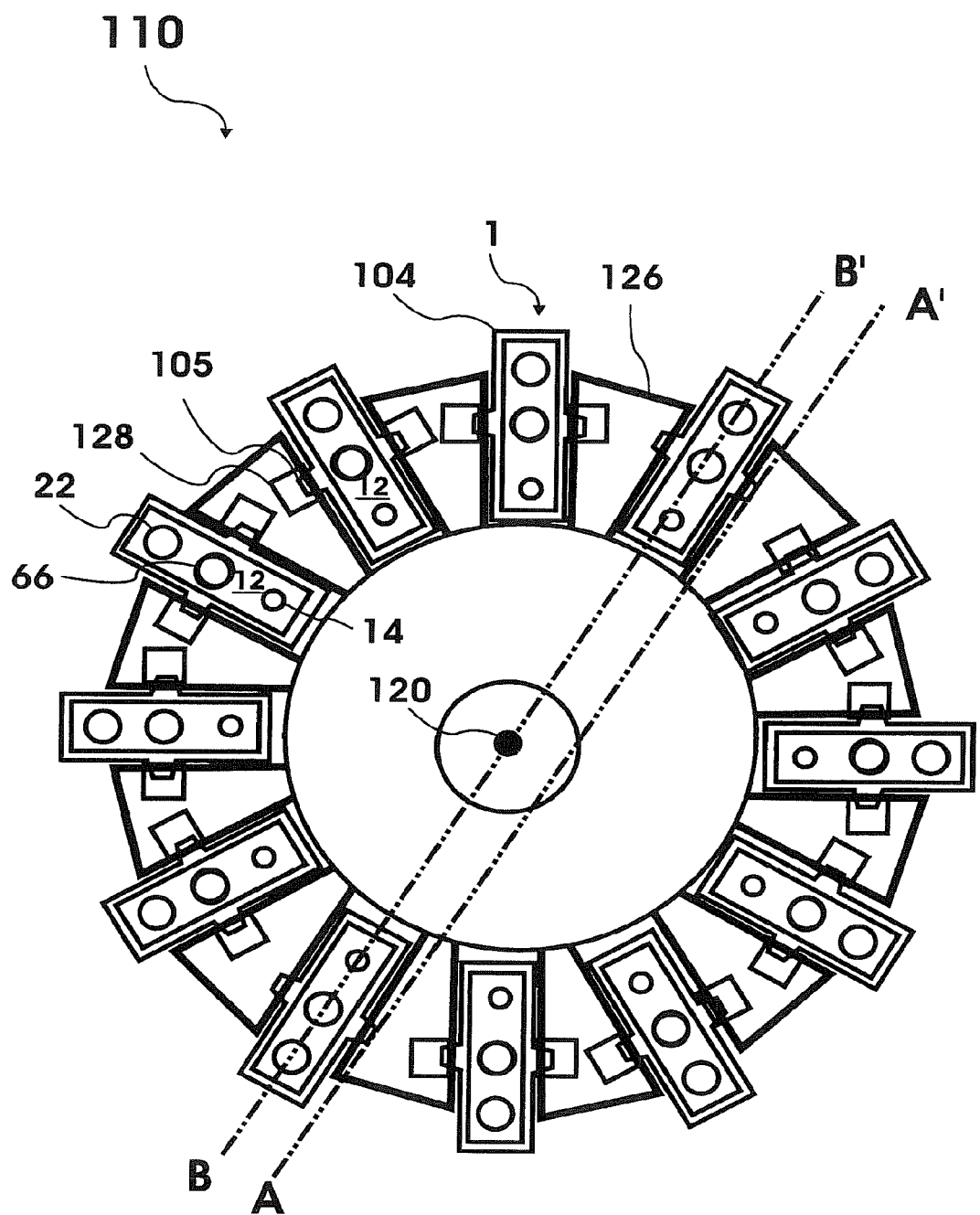
FIG. 17A: A top view of a rotor according to the invention connected to twelve fluid processing devices according to the invention.
Figure 17B:
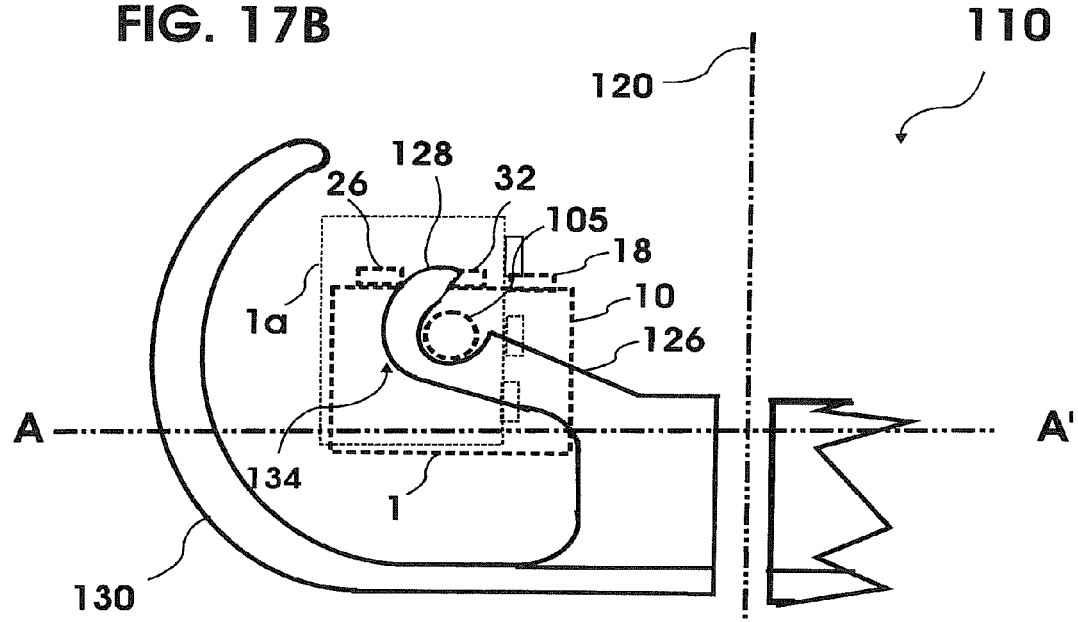
FIG. 17B: A first cross sectional view through the rotor according to the invention illustrating connection means interacting with the swing axle receiver.

FIG. 17A discloses a rotor according to the invention being part of a centrifuge (not shown). As a preferred embodiment this rotor is a rotor 110 for rotating at least one fluid processing device 1 according to the preceding description as well as according to any one of the claims 1 to 73. This rotor 110 comprising rotor connection means 134 for connecting said fluid processing device 1 to said rotor 110 (as shown in FIG. 17B). Further this rotor 110 comprising rotor swing preventing means 132 for limiting a rotation of said fluid processing device 1 around said swinging axis 106 during centrifugation to a predetermined swinging angle (αs), whereby the predetermined swinging angle (αs) is preferably 90 degrees and/or 45 degrees as e.g. described below. FIG. 17A shows rotor 110 carrying twelve identical fluid processing devices 1 of the type, for example, as shown in FIG. 14A-14B with a first tube 18 held by first holder 14, second tube 26 held by second holder 22 and third tube 32 held by third holder 66. First, second and third tubes 18, 26 and 32 are rigidly connected with first container 10 having a first container volume 12. FIG. 17A further discloses connection means 104 for each fluid processing device 1 for connecting the first container comprising structures 103 with respective two rotor arms 126 via swing axle element 105 and its counter part swing axle receiver 128. Swing axle receiver 128 and swing axle element 105 are adapted to each other in such a way that under centrifugal force, fluid processing device 1 swing in outwards direction, i.e. around swinging axis 106 tangentially to the rotation of the rotor rotating around rotation axis 120. Further, since first container comprising structure 103 can be routinely extracted from or inserted into holding structure 102 of connection means 104, connection means 104 may or may not be permanently connected to rotor 110.

Rotor 110 has a rotation axis 120 that may be driven by the centrifuge's motor to a speed exerting a centrifugal force to the fluid processing devices of up to 10,000×g, preferably up to 20,000×g and even up to 50,000×g or more, depending on the application. Further, the invention does not depend on the number of fluid processing devices that can be connected to the rotor at a time, i.e. the number may be one, four, eight, twelve, twenty four or higher depending on the application and the size of the centrifuge.

Figure 17C:
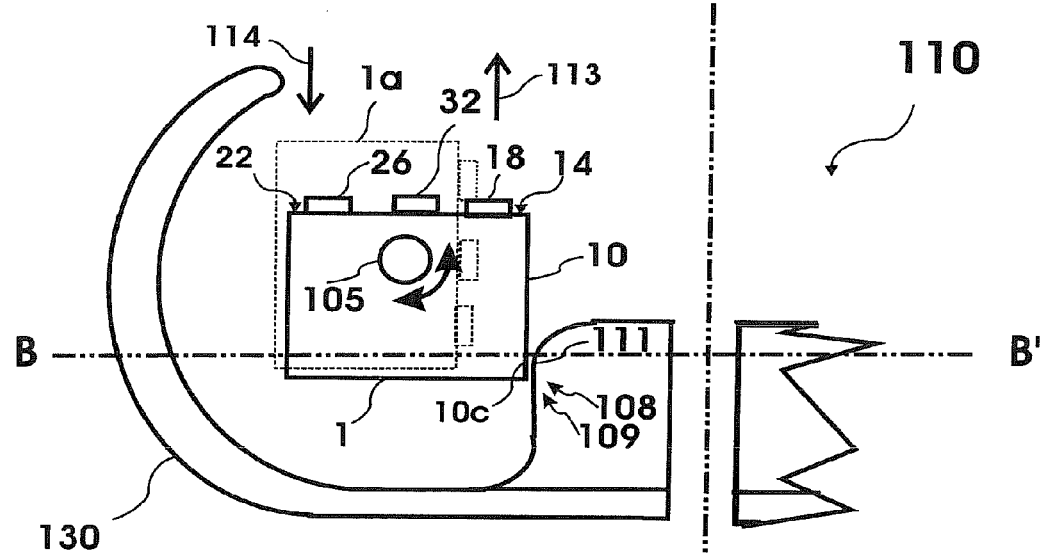
FIG. 17C: A second cross sectional view through the rotor according to the invention illustrating the first and second swing prevention means.

FIGS. 17B-17C illustrate schematically two cross sections through rotor 110 of FIG. 17A along the axes A-A' and B-B' respectively. FIG. 17B shows a cross section along rotor arm 126 holding fluid processing device 1 (first dashed line in bold type) holding a first tube 18, second tube 26 and third tube 32. At rest, first tube 18, second tube 26 and third tube 32 are oriented in gravitational direction. Further, rotor arm 126 radially extends to form a swing axle receiver 128 which serves as a bearing for holding swing axle element 105 of fluid processing device 1. This way, by rotating rotor 110 around rotation axis 120, centrifugal force forces fluid processing device 1 to outwardly rotate around swinging axis 106 (see FIG. 14B). This way, the centrifugal force can exert a pressure on the fluids in the tubes that completely, or to a large extend, points in axial direction of the tubes. FIG. 17B also shows (thin dashed lines) swinging fluid processing device 1a corresponds to fluid processing device 1 at a high rotational speed. In this case, swinging fluid processing device 1a is rotated outwardly around swing axle element 105 by essentially 90 degrees with respect to the fluid processing device's orientation at rest. Fluid processing devices 1 and 1a are drawn in dashed lines since they do not lie within the plane of the cross section of FIG. 17B.

FIG. 17C shows a cross section through rotor 110 along axis B-B' that is slightly shifted with respect to axis A-A' (see FIG. 17A) to cut through fluid processing device 1. FIG. 17C discloses first swing prevention means 108 for preventing a rotation, i.e. swinging, of fluid processing device 1 around swinging axis 106, e.g., during removal of first tube 18 from first holder 14. In the case of FIG. 17C, first swing prevention means 108 acts through an engagement, or touching, of a swing prevention section 10c of first container 10 with rigid swing prevention counterpart 111 that is part of the rotor and coaxially aligned with respect to rotation axis 120. The engagement between swing prevention section 10c and swing prevention counterpart 111 prevents that fluid processing device 1 swings inwardly away due to a first frictional force 113 generated between first tube 18 and first holder 14 during extraction of first tube 18 from first holder 14.

FIG. 17C also discloses second swing prevention means 109 for preventing a rotation of fluid processing device 1 around swinging axis 106, e.g. due to a second frictional force 114 caused by inserting first tube 18 into second holder 22. However, since second holder 22 is positioned on the other side of swing axle element 105 and since second frictional force 114 points in opposite direction with respect to first frictional force 113, second swing prevention means 109 also have to prevent that fluid processing device 1 swings away inwardly. Therefore, in the present case, second swing prevention means 109 and first swing prevention means 108 are the same. Preventing unintended swinging of fluid processing device 1 during transfer of a tube from one holder to the other is an important aspect of the invention when it comes to automation of the transfer process.

Generally, a skilled person will understand that the swing prevention means can be obtained in various other related ways that use a suitable engagement between a swing prevention section and a swing prevention counterpart. Also, while FIG. 17C discloses swing prevention section 10c integrally connected with first container 10, it may be advantageous to have the swing prevention section 10c be part of a holding structure 102 if there is a holding structure 102 for holding first container 10.

Figure 18A:
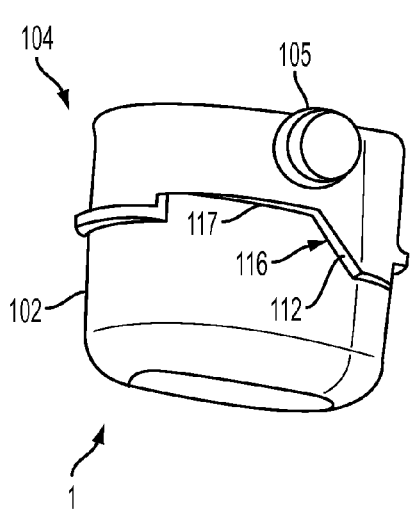
FIG. 18A-18C: A perspective view on a fluid processing device according to the invention having first, second and third swing prevention means.
Figure 18B:
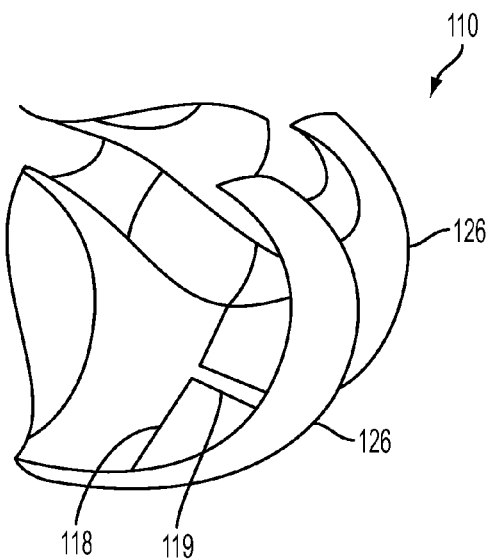
Figure 18C:
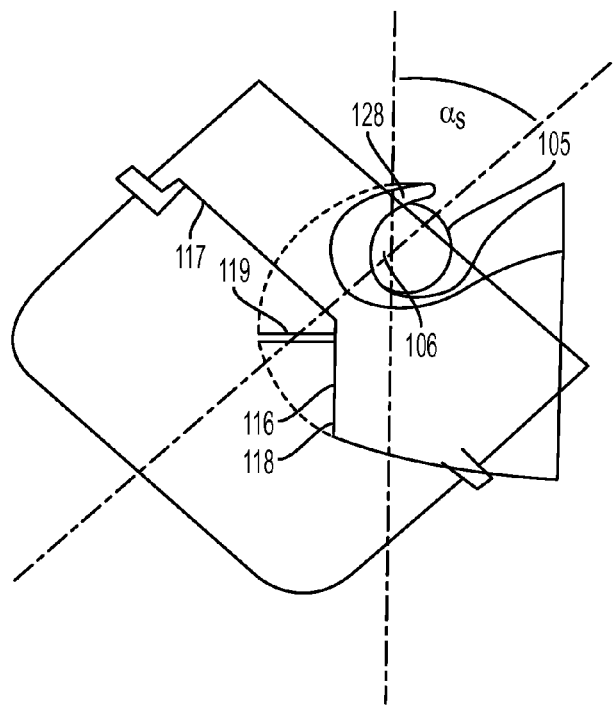

FIGS. 18A-18C illustrate the third swing prevention means 112 for limiting a rotation of fluid processing device 1 around swinging axis 106 during centrifugation to a predetermined swinging angle $\alpha_s$ between the directions given by the first tube at rest and during centrifugation (see FIG. 18C). Swinging axis 106 is defined by respective two swing axle elements 105. Limiting swinging angle $\alpha_s$ is an important aspect of the invention since it has turned out that the filtering effect to fluids may depend on the angle at which the fluid enter the filter element. Therefore, there is a desire to control swinging angle $\alpha_s$.

In the case of FIG. 18A-18C, swinging angle limitation is realized by first edge 116 running in parallel to and protruding from the outer surface of holding structure 102 of connection means 104 (see FIG. 18A). Shape and orientation of first edge 116 are adapted to a second edge 118 running in parallel to and protruding from the surface of an end of rotor arm 126 (see FIG. 18B) in order to engage with each other or to touch each other as soon as during centrifugation, fluid processing device 1 has swung outwardly to predetermined swinging angle αs (see FIG. 18C).

It should be noted that the predetermined swinging angle $\alpha_s$ is adjustable by choosing, for example, between different fluid processing devices having their first edges 116 differently orientated on the surface of the fluid processing device 1. With the first edges 116 having different orientations, the fluid processing devices will engage with the second edge 118 of the rotor 110 at a different swinging angle αs. However, as mentioned before, it is also possible to provide for two different predetermined swinging angles with only one type of fluid processing device 1, or one type of connection means 104. A further example for this concept may be a rotor 110 that has several swing axle receivers 128 for each fluid processing device position wherein each swing axle receiver 128 provides for a different predetermined swinging angle by having differently shaped swing prevention means.

Further, it should be noted that FIGS. 18A-18C also disclose a third edge 117 protruding from the outer surface of first container 10 (or holding structure 102) (see FIG. 18A) whose shape and orientation are adapted to a fourth edge 119 protruding from one side of rotor arm 126 (see FIG. 18B) in order to engage with each other or touch each other as soon as rotor 110 of the centrifuge is at rest. This way, swinging of fluid processing device 1 in inward direction is blocked. Accordingly, third edge 117 and fourth edge 119 represent a further embodiment of the first and second swing prevention means 108, 109 that were described in FIG. 17C.

Figure 19A:
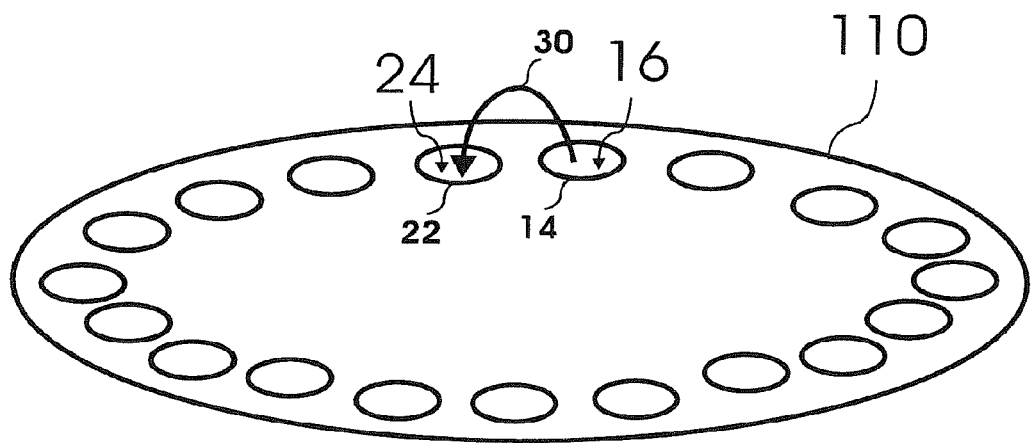
FIG. 19A Schematic illustration of a direct first transfer within a centrifuge in tangential direction FIG. 19B Schematic illustration of a direct first tube transfer within a centrifuge in radial direction FIG. 20A Schematic illustration of a first tube transfer in radial direction from a first holder to a second holder within a fluid processing device according to the invention.
Figure 19B:
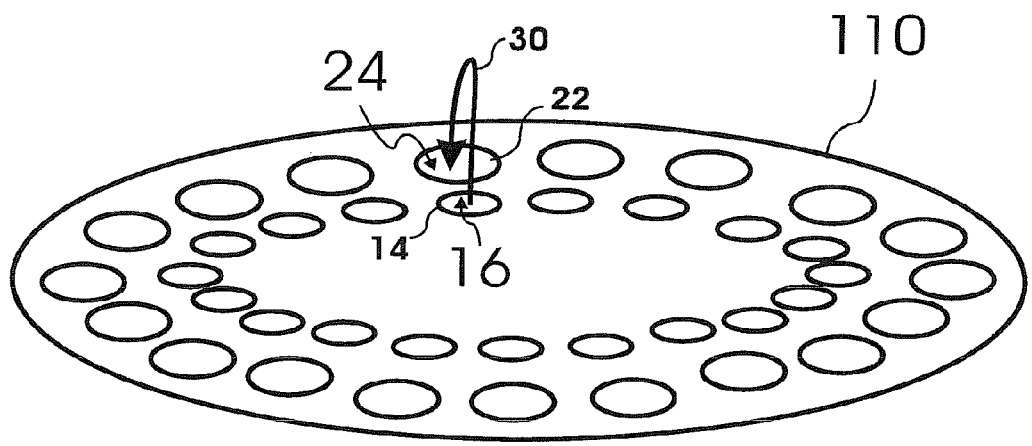

FIGS. 19A-19B schematically disclose two methods according to the invention in which a first tube (not shown) is automatically directly transferred (direct first tube transfer 30) from a first holding position 16 within a centrifuge (not shown) to a second holding position 24 within the centrifuge. In FIG. 19A, the direct first tube transfer 30 is carried out in tangential direction with respect to the rotor's rotation in the centrifuge while in FIG. 19B, the direct first tube transfer 30 is carried out in radial direction with respect to the rotor's rotation in the centrifuge. Preferably, the direct first tube transfer 30 is a transfer from a first holder 14 connected to rotor 110 to a second holder 22 connected to rotor 110. Preferably, this transfer is carried out without that, on its way from first holder 14 to the second holder 22, the first tube is transferred to a third holder that is disconnected from rotor 110, e.g. a holder of a holding rack for holding tubes. With the automated first tube direct transfer 30, it is possible to increase the speed for fluid processing since different fluid processing steps can be carried out directly one after the other without having to transfer the first tube away and back into the centrifuge. For example, with the first tube held by first holder 14, it is possible to carry out the binding or washing steps with a fluid containing biomolecules while discarding the waste fluid into a first container. Then, after the direct transfer 30, with first tube held by second holder 22, it is possible to carry out the elution step in which the eluted fluid is collected in a second container or a second tube for further use.

Figure 20A:
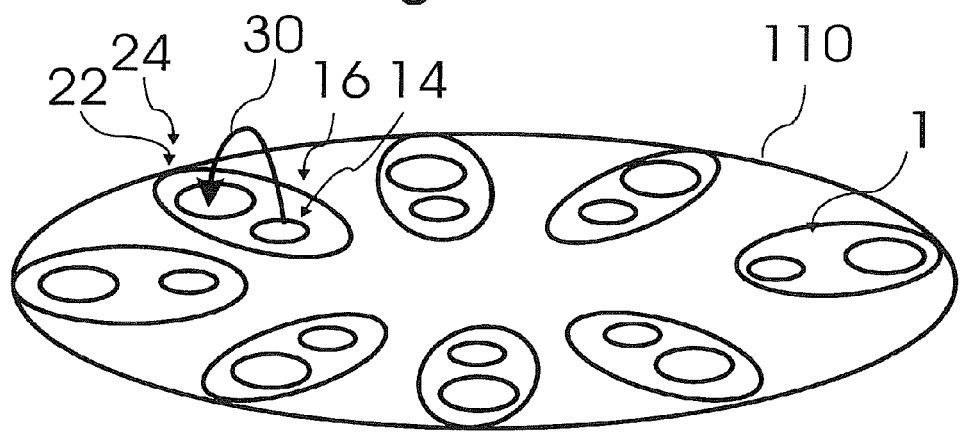
FIG. 20B Schematic illustration of a first tube transfer in tangential direction from a first holder to a second holder within a fluid processing device according to the invention.
FIG. 20C Schematic illustration of a first tube transfer from a first holder of a first fluid processing device according to the invention to a second holder of a second fluid processing device.
FIG. 20D Schematic illustration of a first tube transfer from a first holder of a fluid processing device according to the invention to a position away from the centrifuge and back to a second holder of the fluid processing device.
Figure 20B:
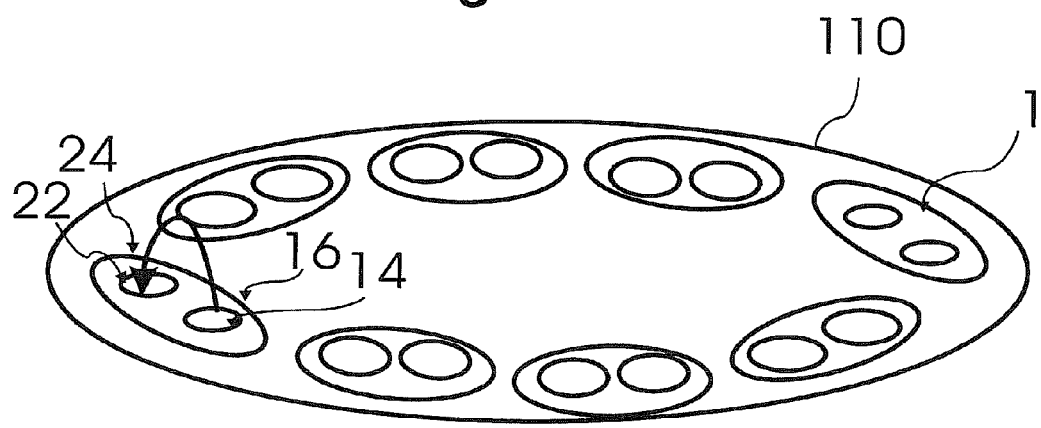
Figure 20C:
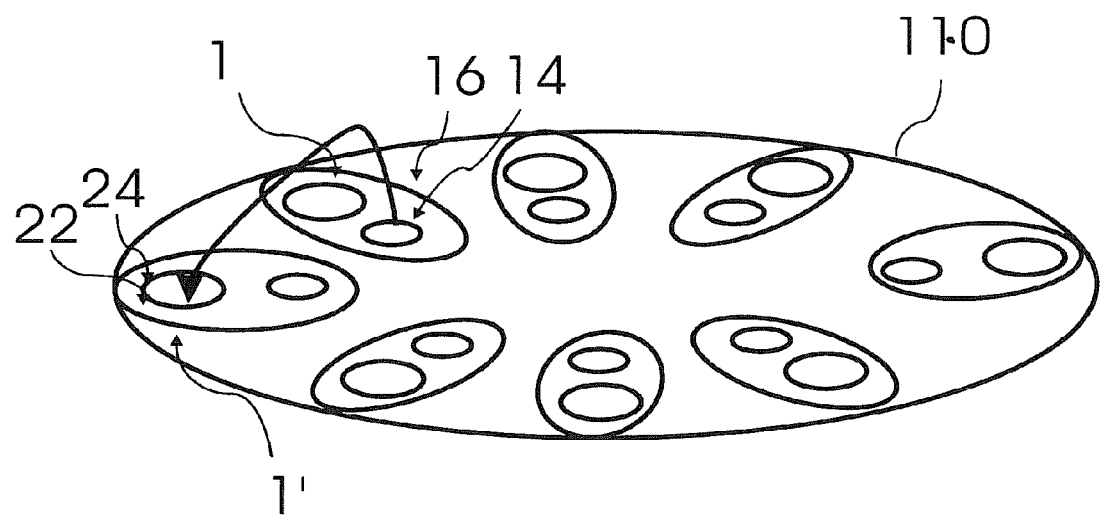
Figure 20D:
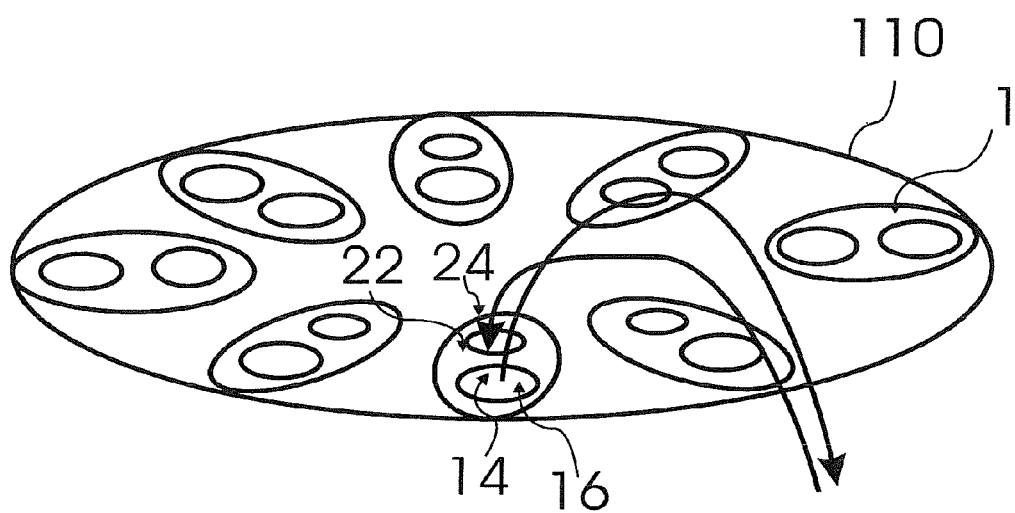

FIGS. 20A-20D schematically disclose further methods according to the invention in which a first tube (not shown) is automatically transferred from a first holder 14 of a fluid processing device 1 according to the invention to a second holder 22 of the same fluid processing device 1 (or of a second fluid processing device 1). In FIG. 20A-20D, eight fluid processing devices 1 according to the invention are disclosed that are connected to rotor 110 which is connected to centrifuge (not shown) that drives the rotor. FIG. 20A discloses a direct transfer from a first holder 14 of a fluid processing device 1 to a second holder 22 of the same fluid processing device 1. Further, the direct transfer is a transfer in radial direction with respect to the rotation of rotor 110. FIG. 20B discloses the same direct transfer as in FIG. 20A with the difference that the respective first and second holders within a fluid processing device 1 are separated in tangential direction with respect to the rotation of rotor 110. FIG. 20C discloses the same direct transfer as in FIG. 20A with the difference that the transfer is carried out from a first holder of a first fluid processing device 1 to a second holder of a second fluid processing device 1' connected to the same rotor 110. FIG. 20D in turn discloses a transfer of a first tube from first holder 14 of a fluid processing device 1 to a position outside of the centrifuge, e.g. to a holder rack, and from there back to second holder 22 of the same or a different fluid processing device 1. However, the transfer may also be a transfer from a first, second or third holder position to a position outside of the centrifuge to, e.g., a waste position, in which case there is no transfer back into the centrifuge to the second holder. The expression "outside of the centrifuge" refers to the opposite of the expression "within the centrifuge". It may relate, for example, to a position where the fluid processing device is disconnected from the rotor, or outside of the centrifuge's protection shield or the like.

In order to carry out the automatic transfer, merely a gripper is required that is capable of engaging and disengaging with the first tube and that can be freely moved in three dimensions in order to transfer the first tube from a first holding position to a second holding position within the centrifuge. Since designing such gripper is within the range of what a person skilled in the art does routinely, no further details on the use and shape of a gripper are given.

Below is an example of a method for processing a fluid using an automated transfer of a first tube from the first holder to the second holder for purifying nucleic acids. The method includes the use of multiple fluid processing devices 1 that each have a first holder 14, a second holder 22, a third holder 66, a first container 10 and a third container 68. The fluid processing devices are compression-moulded in one piece from polymeric material to be light and rigid to withstand centrifugal stress. The first holder 14 is form-fit for holding a first tube 18, e.g. a QIAprep spin column having a filter element 19, e.g. a silica-gel membrane, the second holder 22 is form-fit for holding a second tube 26, e.g. a collection tube (2 ml), and the third holder 66 is empty and used as a third container 68. The tubes are commercially available from the applicant. Note that the outer cross section of the spin column (first tube 18), which at the position where it is held by the first holder 14 is 60.8 mm$^2$ (8.8 mm diameter) is form-fit to the inner cross section of the collection tube (second tube 26). This makes it possible to insert the spin column into the collection tube in a way that the collection tube can hold the spin column during centrifugation and that fluid flowing through the spin column flows into the second container volume 65 of the collection tube. Further, the size of the first container volume 12, i.e. the fluid volume that it can hold during centrifugation without coming into contact with outlet 52 of the first tube 18 or without spilling over the rim of the fluid processing device is approx. 4 ml, of which typically 2 ml are used.

In a first step, the spin columns (first tubes 18) are inserted into the respective first holder 14 of each fluid processing device 1 and the collection tubes (second tubes 26) are inserted into the respective second holder 22 of each fluid processing device 1. In a second step, the fluid processing devices 1 are connected to the rotor 110 of a centrifuge by inserting the fluid processing devices 1 into respective connection means 104. The connection means are adapted for holding a fluid processing device 1 during centrifugation. At the same time, the connection means 104 provide for a swinging connection with rotor 110 to allow each fluid processing device 1 to swing outwardly during centrifugation.

In a third step, various biological samples, e.g resuspended bacterial cells are lysed and neutralised prior to dispensing into the respective third containers 68 of the multiple fluid processing devices within the centrifuge. Subsequently, the multiple fluid processing devices 1 are centrifuged at a centrifugal force equivalent to approx. 12000×g until the cell debris of the various biological samples have been pelleted. Then, the supernatant fractions of the lysates (first fluid) are each withdrawn from respective third containers 68 and dispensed into the respective spin columns (first tubes 18) of the respective fluid processing devices 1.

Then, in order to carry out a binding step, the spin columns (first tubes 18) containing the supernatant fractions are subsequently centrifuged at an acceleration of about 12000×g until the cleared lysates have more or less completely passed through the respective silica-gel membranes. The fluids that have passed through the silica-gel membranes (filter elements 19) are collected in respective first containers 10. At this point, due to the binding property of the silica-gel material to nucleic acid, only the nucleic acids remain with the respective silica-gel membranes.

After the binding step, one or more washing steps are carried out to further purify the nucleic acids bound to the filter elements 19. This is done by dispensing a first reagent, e.g. wash buffers PB, PE (available from Qiagen) into the respective spin columns and by afterwards centrifugating the spin columns (12000×.g for about 1 min) until the first reagent and removed nucleic acid contaminants have passed through the filter elements 19 into the respective first containers 10. This step may be repeated several times with the same or different reagents.

After binding and washing, the respective spin columns (first tubes 18) are automatically withdrawn from respective first holders 14 by a gripper and transferred and placed into respective collection tubes (second tubes 26) that are already in place and held by second holders 22. As a next step, elution fluid (second fluid), e.g. water or elution buffer EB (available from Qiagen) is dispensed into respective spin columns (first tubes 18). This step is followed by a further centrifugation for 1 min at 12000×g until the eluted fluids have passed through the silica-gel membranes (filter elements 19) into the respective collection tubes (second tubes 26). During centrifugation, the elution fluids together with the respective purified nucleic acids are collected in the second tubes 26 of the respective fluid processing devices 1 and ready for further use. Details of the above process are also disclosed in the Protocol: Plasmid DNA Purification Using the QIAprep Spin Miniprep Kit and a Microcentrifuge (QIAGEN QIAprep® Miniprep Handbook, Second Edition, June 2005).

The invention claimed is:

1. A fluid processing device for use in a centrifuge having a rotor, said fluid processing device comprising:
   a) a first holder for holding a first tube having a first cross section; said first holder having a first stopper and said first tube having a first cap; and
   b) at least one first cap fixture means for holding said first cap in a defined position with respect to said first holder during centrifugation in said centrifuge, and
   c) a second holder for holding a second tube, said second holder having a second stopper,
   wherein the first and second holders are cylindrically shaped,
   wherein the first stopper and second stopper extend above and below a surface connecting said first holder and said second holder;
   wherein the at least one first cap fixture means is arranged such that the first cap is held at a position that leaves the first tube's inlet opening open; and
   wherein said at least one first cap fixture means is respectively integral with the first holder.

2. The fluid processing device according to claim 1 whereby said second tube has a second cross section that is different from said first cross section.

3. The fluid processing device according to claim 1 whereby said second holder is form-fit to the shape of said second tube for holding said second tube.

4. The fluid processing device according to claim 1 wherein said second tube is a second container.

5. The fluid processing device according to claim 4 wherein said second container is shaped for holding said first tube so that a fluid flowing through said first tube flows into said second container.

6. The fluid processing device according to claim 1 comprising at least one second cap fixture means for holding a second cap of said second tube during centrifugation.

7. The fluid processing device according to claim 1 whereby said at least one first cap fixture means includes a cap enclosure structure for partially enclosing the first cap during centrifugation.

8. The fluid processing device according to claim 1 wherein during centrifugation, at least one of said first tube and said second tube are exposed to an acceleration of at least 100 g.

9. The fluid processing device according to claim 1 wherein during centrifugation, at least one of said first tube and said second tube are exposed to an acceleration of at least 1000 g.

10. The fluid processing device according to claim 1 wherein during centrifugation, at least one of said first tube and said second tube are exposed to an acceleration of at least 10000 g.

11. The fluid processing device according to claim 1 comprising connection means for removably connecting said fluid processing device with the rotor of said centrifuge.

12. The fluid processing device according to claim 1 wherein said fluid processing device is made of one piece.

* * * * *